US012268607B2

(12) United States Patent
Gordon et al.

(10) Patent No.: US 12,268,607 B2
(45) Date of Patent: Apr. 8, 2025

(54) COMPUTER-ASSISTED CRANIOPLASTY

(71) Applicant: THE JOHNS HOPKINS UNIVERSITY, Baltimore, MD (US)

(72) Inventors: Chad R. Gordon, Baltimore, MD (US); Mehran Armand, Baltimore, MD (US); Gerald T. Grant, Baltimore, MD (US); Peter Liacouras, Baltimore, MD (US); Ryan Murphy, Baltimore, MD (US); Kevin Wolfe, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 17/511,987

(22) Filed: Oct. 27, 2021

(65) Prior Publication Data
US 2022/0257383 A1    Aug. 18, 2022

Related U.S. Application Data

(63) Continuation of application No. 15/529,036, filed as application No. PCT/US2015/062521 on Nov. 24, 2015, now abandoned.
(Continued)

(51) Int. Cl.
*A61F 2/30* (2006.01)
*A61B 34/10* (2016.01)
(Continued)

(52) U.S. Cl.
CPC .......... *A61F 2/30942* (2013.01); *A61B 34/10* (2016.02); *A61B 34/20* (2016.02);
(Continued)

(58) Field of Classification Search
CPC .. A61F 2/30942; A61F 2/3094; A61F 2/2875; A61F 2002/30948; A61B 34/10;
(Continued)

(56) References Cited

U.S. PATENT DOCUMENTS 3,457,922 A  7/1969 Ray
4,436,684 A  3/1984 White
(Continued)

FOREIGN PATENT DOCUMENTS

CN    101528158 A    9/2009
WO    2012147114 A1  11/2012
(Continued)

OTHER PUBLICATIONS

International Search Report and Written Opinion in International Application No. PCT/US2015/062521, 12 pages.
(Continued)

*Primary Examiner* — Joel Lamprecht
*Assistant Examiner* — Amy Shafqat
(74) *Attorney, Agent, or Firm* — MH2 Technology Law Group LLP

(57) ABSTRACT

Provided is a surgical method. The method includes detecting a location of a reference unit having a trackable element with a detector, the detector configured to provide at least one signal corresponding to a detected location of at least the reference unit's trackable element; accessing a computer-readable reconstruction of the being's anatomy; accessing a computer-readable reconstruction of an implant; detecting a location of a pointer tool comprising a trackable element with the detector, where the pointer tool is associated with a location of an anatomical feature of interest; accessing at least one computer-readable reconstruction of a trace, the trace corresponding to a geometry of the anatomical feature of interest; and superimposing the at least one updatable, computer-readable trace on the second computer-readable reconstruction of the implant.

8 Claims, 16 Drawing Sheets

Related U.S. Application Data

(60) Provisional application No. 62/117,782, filed on Feb. 18, 2015.

(51) Int. Cl.
*A61B 34/20* (2016.01)
*A61B 90/00* (2016.01)
*A61F 2/28* (2006.01)

(52) U.S. Cl.
CPC .......... *A61F 2/2875* (2013.01); *A61F 2/3094* (2013.01); *A61B 2034/104* (2016.02); *A61B 2034/108* (2016.02); *A61B 2034/2055* (2016.02); *A61B 2034/2057* (2016.02); *A61B 2034/2068* (2016.02); *A61B 2090/395* (2016.02); *A61B 2090/3979* (2016.02); *A61F 2002/30948* (2013.01)

(58) Field of Classification Search
CPC ............ A61B 34/20; A61B 2034/2055; A61B 2090/3979; A61B 2034/2057; A61B 2034/104; A61B 2090/395; A61B 2034/2068; A61B 2034/108
See application file for complete search history.

(56) References Cited

U.S. PATENT DOCUMENTS

| | | | |
|---|---|---|---|
| 5,279,575 A | 1/1994 | Sugarbaker | |
| 5,741,215 A | 4/1998 | DUrso | |
| 5,810,712 A | 9/1998 | Dunn | |
| 5,951,498 A | 9/1999 | Arnett | |
| 6,079,681 A | 6/2000 | Stern et al. | |
| 6,112,109 A | 8/2000 | DUrso | |
| 6,120,290 A | 9/2000 | Fukushima et al. | |
| 6,226,548 B1 | 5/2001 | Foley et al. | |
| 6,254,639 B1 | 7/2001 | Peckitt | |
| 6,285,902 B1 | 9/2001 | Ill et al. | |
| 6,491,699 B1 | 12/2002 | Henderson et al. | |
| 6,500,179 B1 | 12/2002 | Masini | |
| 6,608,628 B1 | 8/2003 | Ross et al. | |
| 6,726,678 B1 | 4/2004 | Nelson et al. | |
| 6,796,986 B2 | 9/2004 | Duffner | |
| 6,845,175 B2 | 1/2005 | Kopelman et al. | |
| 6,932,842 B1* | 8/2005 | Litschko | G05B 19/4099 623/901 |
| 7,050,877 B2 | 5/2006 | Iseki et al. | |
| 7,113,841 B2 | 9/2006 | Abe et al. | |
| 7,510,557 B1* | 3/2009 | Bonutti | A61F 2/3859 606/86 R |
| 7,596,399 B2 | 9/2009 | Singhal et al. | |
| 7,747,305 B2 | 6/2010 | Dean et al. | |
| 7,747,318 B2 | 6/2010 | John et al. | |
| 7,792,341 B2 | 9/2010 | Schutyser | |
| 7,857,821 B2 | 12/2010 | Couture et al. | |
| 7,953,260 B2 | 5/2011 | Weinzweig et al. | |
| 8,086,336 B2 | 12/2011 | Christensen | |
| 8,096,997 B2 | 1/2012 | Plaskos et al. | |
| 8,221,430 B2 | 7/2012 | Park et al. | |
| 8,221,461 B2 | 7/2012 | Kuiper et al. | |
| 8,357,165 B2 | 1/2013 | Grant et al. | |
| 8,397,732 B2 | 3/2013 | Singhal et al. | |
| 8,403,934 B2 | 3/2013 | Angibaud et al. | |
| 8,428,315 B2 | 4/2013 | Suetens et al. | |
| 8,518,085 B2 | 8/2013 | Winslow et al. | |
| 8,535,063 B1 | 9/2013 | Amato | |
| 8,650,005 B2 | 2/2014 | Liao | |
| 8,706,285 B2 | 4/2014 | Narainasamy et al. | |
| 8,781,557 B2 | 7/2014 | Dean et al. | |
| 8,827,932 B2 | 9/2014 | Hirabayashi | |
| 9,208,558 B2 | 12/2015 | Dean et al. | |
| 9,216,084 B2 | 12/2015 | Gordon et al. | |
| 9,330,206 B2 | 5/2016 | Dean et al. | |
| 9,659,152 B2 | 5/2017 | Mueller | |
| 10,537,337 B2 | 1/2020 | Gordon et al. | |
| 2001/0021851 A1 | 9/2001 | Eberlein et al. | |
| 2001/0027271 A1* | 10/2001 | Franck | A61B 90/11 606/130 |
| 2002/0035458 A1 | 3/2002 | Kim et al. | |
| 2002/0165552 A1 | 11/2002 | Duffner | |
| 2002/0169485 A1 | 11/2002 | Pless et al. | |
| 2004/0091845 A1 | 5/2004 | Azerad et al. | |
| 2004/0172044 A1 | 9/2004 | Grimm et al. | |
| 2004/0204760 A1 | 10/2004 | Fitz et al. | |
| 2005/0043835 A1 | 2/2005 | Christensen | |
| 2005/0113846 A1 | 5/2005 | Carson | |
| 2005/0117696 A1 | 6/2005 | Suzuki et al. | |
| 2006/0142657 A1 | 6/2006 | Quaid et al. | |
| 2006/0195111 A1 | 8/2006 | Couture | |
| 2007/0167701 A1 | 7/2007 | Sherman | |
| 2007/0207441 A1 | 9/2007 | Lauren | |
| 2007/0225773 A1 | 9/2007 | Shen et al. | |
| 2008/0140149 A1 | 6/2008 | John et al. | |
| 2008/0304725 A1 | 12/2008 | Lietner | |
| 2008/0306490 A1 | 12/2008 | Lakin et al. | |
| 2008/0319448 A1 | 12/2008 | Lavallee et al. | |
| 2009/0088674 A1 | 4/2009 | Caillouette et al. | |
| 2009/0092948 A1 | 4/2009 | Gantes | |
| 2009/0099570 A1 | 4/2009 | Paradis et al. | |
| 2009/0112273 A1 | 4/2009 | Wingeier et al. | |
| 2009/0220122 A1 | 9/2009 | Richards et al. | |
| 2009/0240141 A1 | 9/2009 | Neubauer et al. | |
| 2009/0281623 A1 | 11/2009 | Kast et al. | |
| 2009/0311647 A1 | 12/2009 | Fang et al. | |
| 2010/0145425 A1 | 6/2010 | Jung et al. | |
| 2010/0145898 A1 | 6/2010 | Malfliet et al. | |
| 2010/0261998 A1 | 10/2010 | Stiehl | |
| 2010/0311028 A1 | 12/2010 | Albert et al. | |
| 2011/0029093 A1 | 2/2011 | Bojarski et al. | |
| 2011/0066072 A1 | 3/2011 | Kawoos et al. | |
| 2011/0087465 A1 | 4/2011 | Mahfouz | |
| 2011/0102549 A1 | 5/2011 | Takahashi | |
| 2011/0117530 A1 | 5/2011 | Albocher et al. | |
| 2011/0196377 A1* | 8/2011 | Hodorek | A61B 17/155 606/87 |
| 2011/0208256 A1 | 8/2011 | Zuhars | |
| 2011/0244415 A1 | 10/2011 | Batesole | |
| 2012/0041318 A1 | 2/2012 | Taylor | |
| 2012/0041446 A1 | 2/2012 | Wong et al. | |
| 2012/0063655 A1 | 3/2012 | Dean et al. | |
| 2012/0109228 A1 | 5/2012 | Boyer et al. | |
| 2012/0230568 A1 | 9/2012 | Grbic et al. | |
| 2012/0259592 A1 | 10/2012 | Liao | |
| 2013/0035690 A1 | 2/2013 | Mittelstadt et al. | |
| 2013/0122463 A1 | 5/2013 | Csillag | |
| 2013/0204600 A1 | 8/2013 | Mehra | |
| 2013/0211424 A1 | 8/2013 | Thiran et al. | |
| 2013/0211792 A1 | 8/2013 | Kang et al. | |
| 2013/0217996 A1 | 8/2013 | Finkelstein et al. | |
| 2013/0296872 A1 | 11/2013 | Davison et al. | |
| 2013/0297265 A1 | 11/2013 | Baloch et al. | |
| 2013/0310963 A1 | 11/2013 | Davison | |
| 2014/0045167 A1 | 2/2014 | Anderson et al. | |
| 2014/0122382 A1 | 5/2014 | Elster et al. | |
| 2014/0127639 A1 | 5/2014 | Hirabayashi | |
| 2014/0267631 A1* | 9/2014 | Powers | H04N 23/80 348/47 |
| 2014/0329194 A1 | 11/2014 | Sachdeva et al. | |
| 2014/0343557 A1 | 11/2014 | Mueller | |
| 2015/0272691 A1 | 10/2015 | Kim et al. | |
| 2015/0297309 A1 | 10/2015 | Bly et al. | |
| 2015/0328004 A1* | 11/2015 | Mafhouz | G05B 19/4099 700/98 |
| 2016/0038243 A1 | 2/2016 | Miller et al. | |
| 2016/0045317 A1 | 2/2016 | Ang et al. | |
| 2016/0324664 A1* | 11/2016 | Piron | A61F 2/4601 |
| 2016/0342766 A1* | 11/2016 | Darwood | A61B 17/17 |
| 2016/0346091 A1 | 12/2016 | Bin Abdul Rahman et al. | |
| 2017/0014169 A1 | 1/2017 | Dean et al. | |

(56) References Cited

U.S. PATENT DOCUMENTS

| | | |
|---|---|---|
| 2017/0108930 A1 | 4/2017 | Banerjee et al. |
| 2017/0273797 A1 | 9/2017 | Gordon et al. |

FOREIGN PATENT DOCUMENTS

| | | |
|---|---|---|
| WO | 2013101753 A1 | 7/2013 |
| WO | 2014043452 A1 | 3/2014 |

OTHER PUBLICATIONS

Jalbert et al., "One-step primary reconstruction for complex craniofacial re section with PEEK custom-made implants", Journal of Cranio-Maxillo-Facial Surgery, Mar. 2014, vol. 42, No. 2, pp. 141-148.

Murphy et al., "Computer-assisted single-stage cranioplasty", IN: Engineering in Medicine and Biology Sociaty (EMBC), Aug. 25-29, 2015, pp. 4910-4912.

Non-Final Office Action in corresponding U.S. Appl. No. 16/707,551 mailed on May 12, 2021, 6 pages.

Bell, R. B., "Computer Planning and Intraoperative Navigation in Orthognathic Surgery"; Journal of Oral and Maxillofacial Surgery; 2011, vol. 69, No. 3, pp. 592-605.

Cevidances, L. et al. Three-dimensional surgical simulation:, American Journal of Orhodontics and Dentofacial Orhopedics, vol. 138, Issue 3, Sep. 2010, pp. 361-371 (Year:2010).

Chapuis et al., "A new approach for 3D computer-assisted orthognathic surgery-first clinical case", Elsevier, International Congress Serier, vol. 1281, May 2005, pp. 1217-1222 (Year: 2005).

Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).

Extended European Search Report dated Jul. 27, 2018 in corresponding EP Application No. 15862375, 8 pages.

Extended European Search Report dated May 24, 2018 in corresponding EP Application No. 15862868, 8 pages.

Goh, R. et al., "Customized fabricated implats after previous failed cranioplasty", Journal of Plastic, Reconstructive and Aesthetic Surgery, vol. 63, 2010, pp. 1479-1484.

Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.

International Search Report and Written Opinion dated Mar. 9, 2015 from corresponding International Application No. PCT/US2014/067671; 13 pages.

International Search Report and Written Opinion in International Application No. PCT/US2015/062516, 10 pages.

International Search Report and Written Opinion mailed Sep. 12, 2016 for PCT/US2016/030447.

International Search Report dated Feb. 24, 2015 from corresponding International Application No. PCT/US2014/067504; 5 pgs.

International Search Report dated Mar. 13, 2015 from corresponding International Application No. PCT/US2014/067167; 5 pgs.

International Search Report dated Mar. 20, 2015 from corresponding International Application No. PCT/US2014/067692; 4 pgs.

International Search Report dated Mar. 5, 2015 from corresponding International Application No. PCT/US2014/067174; 4 pgs.

International Search Report dated Mar. 5, 2015 from corresponding International Application No. PCT/US2014/067656; 5 pgs.

International Search Reported dated Feb. 24, 2015 from corresponding International Application No. PCT/US2014/067504; 11 pgs.

International Search Reported dated Feb. 27, 2015 from corresponding International Application No. PCT/US2014/067581; 4 pgs.

Lee, M. et al., "Custom implant design for patients with craniel defects", Engineering in Medicine and Biology Magazine, IEEE, 2002, vol. 21, pp. 38-44.

Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.

Murphy et al. "Computer-Assisted, Le Fort-Based, Face-Jaw-Teeth Transplantation: A Pilot Study on System Feasibility and Translational Assessment." International journal of computer assisted radiology and surgery, 2014.

Schramm et al.; "Non-invasive Registration in Computer Assisted Craniomaxillofacial Surgery"; Rechner-und Sensorgestutzte Chirurgie, 2001, pp. 258-268.

Examination Report in Australian Corresponding Application No. 2015353601 dated Jul. 29, 2019, 4 pages.

Examination Report in Australian Corresponding Application No. 2015353523 dated Jun. 28, 2019, 3 pages.

Extended European Search Report in Corresponding EP Application No. 16842453 dated Apr. 16, 2019, 8 pages.

Final Office Action in U.S. Appl. No. 15/100,229 dated Oct. 21, 2019, 48 pages.

Final Office Action in U.S. Appl. No. 15/100,241 dated Aug. 15, 2019, 27 pages.

Non Final Office Action n U.S. Appl. No. 15/100,252 dated Sep. 25, 2019, 9 pages.

Notice of Allowance in U.S. Appl. No. 15/100,258 dated Sep. 11, 2019, 6 pages.

Final Office Action in U.S. Appl. No. 15/529,042 dated Sep. 4, 2019, 9 pages.

Non Final Office Action in U.S. Appl. No. 15/100,256 dated Jun. 14, 2019, 13 pages.

\* cited by examiner

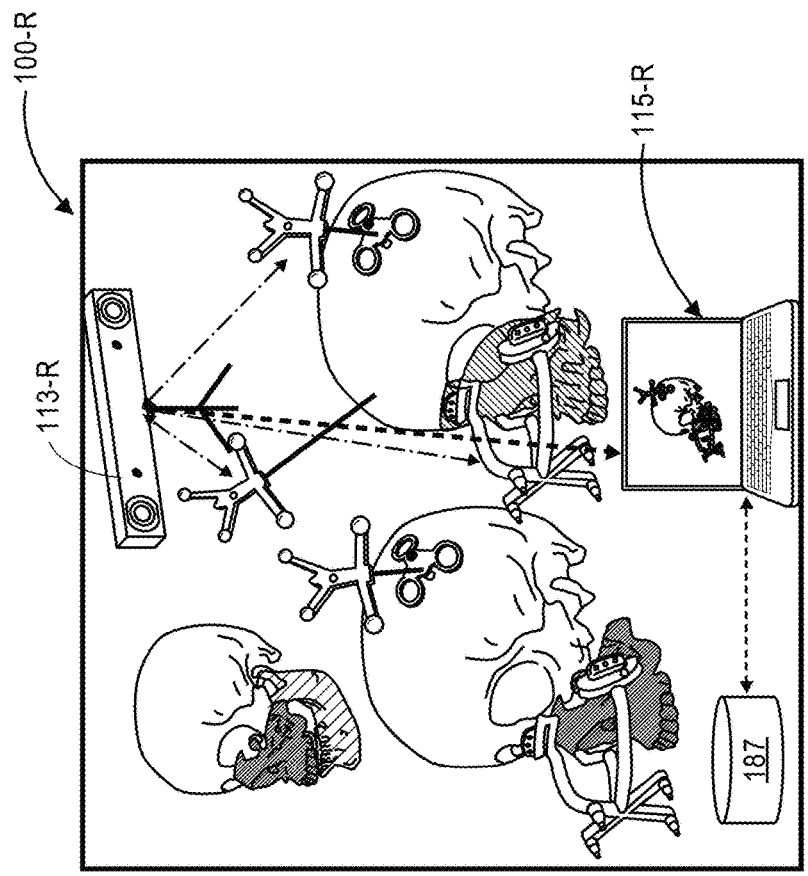
FIG. 1C
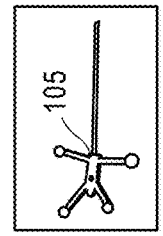
FIG. 1D
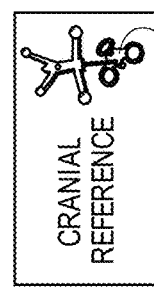
FIG. 1E
FIG. 1F
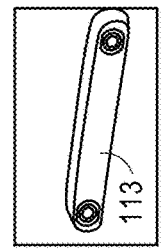
FIG. 1G
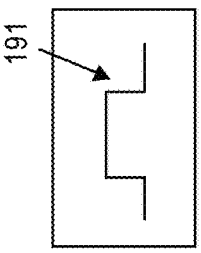
FIG. 1H

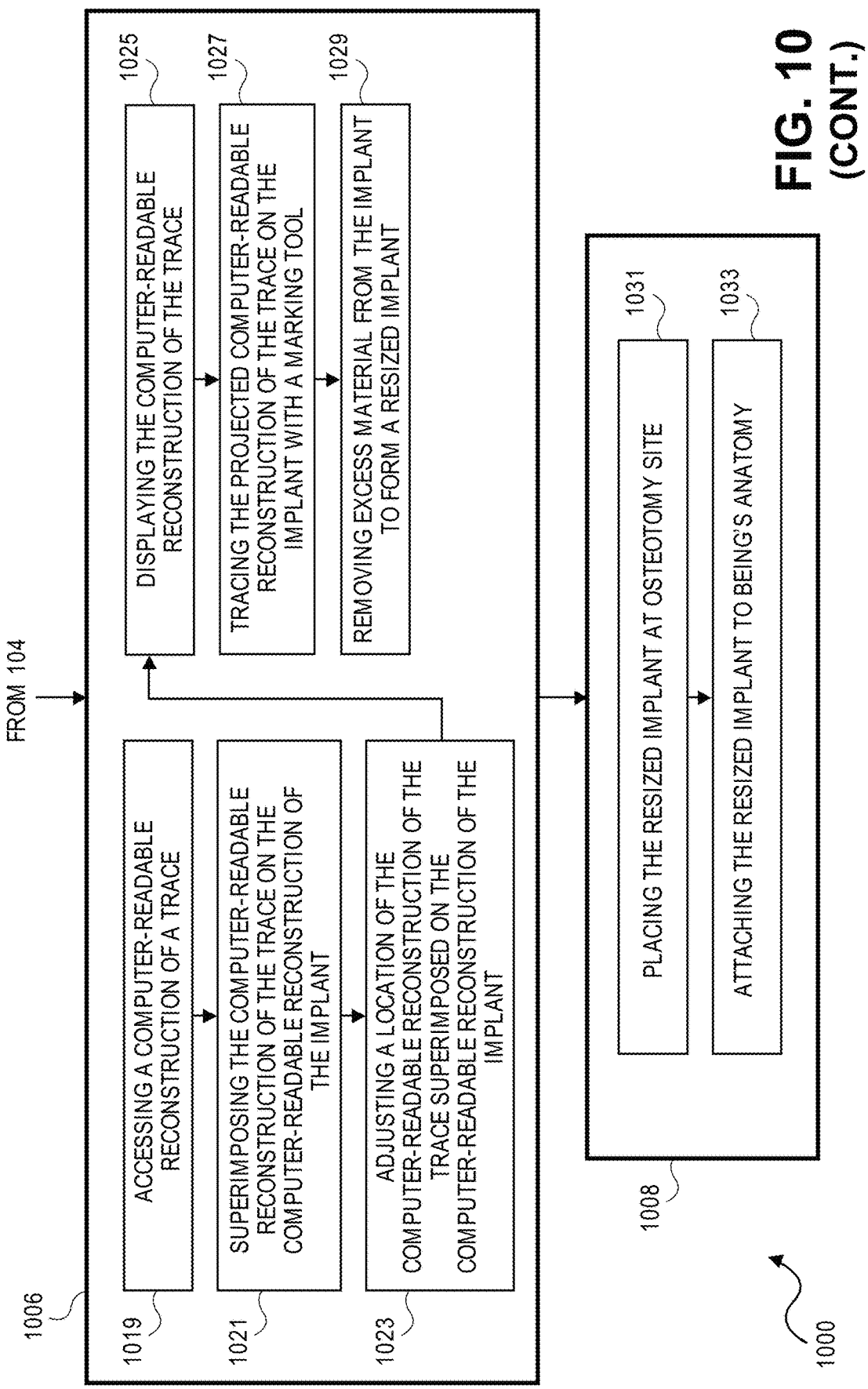

COMPUTER-ASSISTED CRANIOPLASTY

CROSS-REFERENCE TO RELATED APPLICATIONS

This application is a continuation of U.S. application Ser. No. 15/529,036 filed May 23, 2017, which is a national stage entry of International Patent Application No. PCT/US2015/062521 filed Nov. 24, 2015, which claims the benefit of U.S. Provisional Patent Application Ser. No. 62/117,782, filed on Feb. 18, 2015, the entirety of all of which are incorporated herein by reference.

GOVERNMENT RIGHTS

This invention was made with government support under NCATS Grant No. UL1TR000424-06 awarded by the National Institutes of Health. The government has certain rights in the invention.

FIELD

The embodiments described herein relate generally to the field of surgery, particularly cranioplasty and craniomaxillofacial surgery, and specifically to the field of computer-assisted surgery.

BACKGROUND

Craniectomies requiring cranioplasty are either decompressive following stroke/trauma—or occur as a result of oncological ablation for masses involving the bony calvarium. In the setting of trauma with cerebral edema, stroke with bleeding, or autologous bone flap infections requiring removal, delayed cranioplasties are necessary at a secondary stage. Nearly 250,000 primary brain tumors/skull-based neoplasms are diagnosed each year resulting in a range of 4500-5000 second-stage implant cranioplasties/year.

Craniectomy defects following resection of calvarial lesions are most often reconstructed using on-table manufacturing, as similar to all defects in the craniomaxillofacial skeleton. For tumor ablative surgery—where tumors and/or processes involve the bony calvarium—cranioplasties are most often performed primarily using suboptimal hand-molding techniques. Currently, the standard of care is to reconstruct the cranial defects with on-table manipulation using a varying combination of materials. For example, oncological defects are commonly reconstructed with "off-the-shelf" materials, as opposed to using a pre-fabricated customized implant—simply because the exact defect size/shape is unknown. A variety of materials may be used to reconstruct large cranial defects, including titanium mesh, porous hydroxyapatite (HA), polymethylmethacrylate (PMMA), and polyether ether ketone (PEEK), among others.

Some of these materials can be molded and/or shaped in the operating room to approximate concave defects—especially in instances greater than 5 cm squared in size. Of note, the most frequently used material next to titanium mesh is liquid PMMA, which is used alone for small defects and/or in conjunction with titanium mesh for larger defects. It is affordable, time-tested and easy to use. However, on-table manipulation results in some form of craniofacial asymmetry and a post-operative appearance which is suboptimal. Furthermore, the difficult shaping process may take several hours—which in turn increases anesthesia, total blood loss, risk for infection, morbidity, and all costs associated with longer operative times.

With the advent of computer-aided design/manufacturing (CAD/CAM) and customized craniofacial implants (CCIs), more suited alternatives are available. Thus, CAD/CAM adds another dimension to the material chosen for reconstruction, for example, by allowing one to match the contralateral, non-operated side for ideal contour and appearance. With CAD/CAM fabrication, near-perfectly shaped CCIs can be ordered and pre-fabricated based on fine cut preoperative computed tomography (CT) scans and three-dimensional reconstruction (+/−stereolithographic models). In fact, recent reports suggest that CCI's have the ability to improve cosmesis, decrease operative times and enhance patient satisfaction.

In the literature, there are only a few case reports where immediate reconstructions with CCI's were performed for benign skull neoplasms following resection (i.e. meningioma, fibrous dysplasia). While studies have reported favorable results and acceptable outcomes, there is a trend towards decreased operative times, and less overall surgery—by avoiding revision surgery. In cases of malignant neoplasms involving the bony calvarium, secondary cranioplasty (after surgical margins have been cleared) is advocated. However, there is only one successful case report of immediate CCI reconstruction following resection of a Ewing sarcoma.

Historically, cranioplasties with such CCIs can only be performed as second stage operations during which a clinician, such as a surgeon, ensures that the CCI fits perfectly into the skull defect. The recent developments have demonstrated the feasibility of CCIs for "single-stage cranioplasty", but this involves using a handheld bur to shave down the pre-fabricated implant artistically. However, challenges in both assessing and predicting each tumor-resection deformity pre-surgery still limits the applicability of CCIs in this patient population. For example, challenges such as 1) unknown exact tumor size, 2) unknown growth from time of pre-op CT scan-to-actual day of surgery, and 3) the unknown resection margins needed to minimize local recurrence. Thus, in the typical case, the implant is designed preoperatively knowing that the neoplasm may be larger (i.e. may have grown in the interim, more invasive to the surrounding tissues, etc.) than the pre-op radiographic imaging depicts, which means removing more normal tissue along the periphery to help minimize local tumor recurrence. In some cases, surgeons may resect the diseased bone using a cutting template (i.e. pre-fabricated guide) to help eradicate the need for intra-operative modification and additional labor, but this technique does not follow true oncological principle—since the tumor resection should be limitless and ideally based on visual evaluation, rather than the pre-operative radiographic study. For these cases, the CCI would need to be reshaped/resized intraoperatively from a size slightly larger than expected—which is a process that may take, on average, between 10-80 minutes.

Accordingly, use of a computer-assisted surgical system of an embodiment may significantly reduce the intraoperative time used for reshaping/resizing the customized implant. However, with no established planning and execution systems available to assist these single-stage reconstructions, a technology and/or surgical method that allows surgeons to resize, adjust, modify or trim alloplastic or bio-engineered implants during surgery to fit the surgical cuts, defects, and/or pre-existing deformities requiring complex reconstruction, or generally overcome the limitations of current technology and surgical methods, would be welcome in the art.

SUMMARY

In an embodiment, there is a surgical method. The method includes detecting a location of a reference unit having a trackable element with a detector, the detector configured to provide at least one signal corresponding to a detected location of at least the reference unit's trackable element, wherein the reference unit is associated with a location of an anatomical feature of a being's anatomy; accessing a computer-readable reconstruction of the being's anatomy, the computer-readable reconstruction of the being's anatomy having a first updatable orientation, wherein the first updatable orientation is updated in response to the at least one signal; accessing a computer-readable reconstruction of an implant having a second updatable orientation; detecting a location of a pointer tool comprising a trackable element with the detector, the detector further configured to provide at least one other signal corresponding to a detected location of at least the pointer tool, wherein the pointer tool is associated with a location of an anatomical feature of interest; accessing at least one computer-readable reconstruction of a trace, the trace corresponding to a geometry of the anatomical feature of interest based on updated detected locations of the pointer tool; superimposing the at least one updatable, computer-readable trace on the second computer-readable reconstruction of the implant.

In another embodiment, there is a method of sizing an implant to an anatomical feature. The method includes generating at least one computer-readable reconstruction of a being's anatomy with a first source, wherein the at least one computer-readable reconstruction of the being's anatomy includes position information corresponding to an orientation of the first source; accessing the at least one computer-readable reconstruction of the being's anatomy and position information; displaying an image based on the at least one computer-readable reconstruction of the being's anatomy and the position information; and superimposing the displayed image onto an object.

Additional advantages of the embodiments will be set forth in part in the description which follows, and in part will be understood from the description, or may be learned by practice of the embodiment(s). The advantages will be realized and attained by means of the elements and combinations particularly pointed out in the appended claims.

It is to be understood that both the foregoing general description and the following detailed description are exemplary and explanatory only and are not restrictive of the embodiment(s), as claimed.

The accompanying drawings, which are incorporated in and constitute a part of this specification, illustrate embodiments described herein and together with the description, serve to explain the principles of the embodiments.

BRIEF DESCRIPTION OF THE DRAWINGS

FIGS. 1A-1C provide schematic overviews of a computer-assisted surgical system.

FIGS. 1D-1H are graphical reconstructions of some components and/or features of the surgical system of FIGS. 1A-1C.

In FIG. 9A, an anatomical feature of interest (e.g., a defect) is identified. In FIG. 9B, an oversized implant (with four tabs for mounting and image alignment) is shown with a trace/image of a patient's anatomical defect generated according to an embodiment (i.e., a resected overlay) is superimposed/projected on the surface of the implant. In FIG. 9B, a surgeon traces the projected resected overlay with a sterile marking pen directly onto a surface of the implant and then shaves off excess implant material. In FIG. 9D, the resized implant is shown attached to the resected surface of the being's anatomy.

DETAILED DESCRIPTION OF THE EMBODIMENTS

Figure 1A:
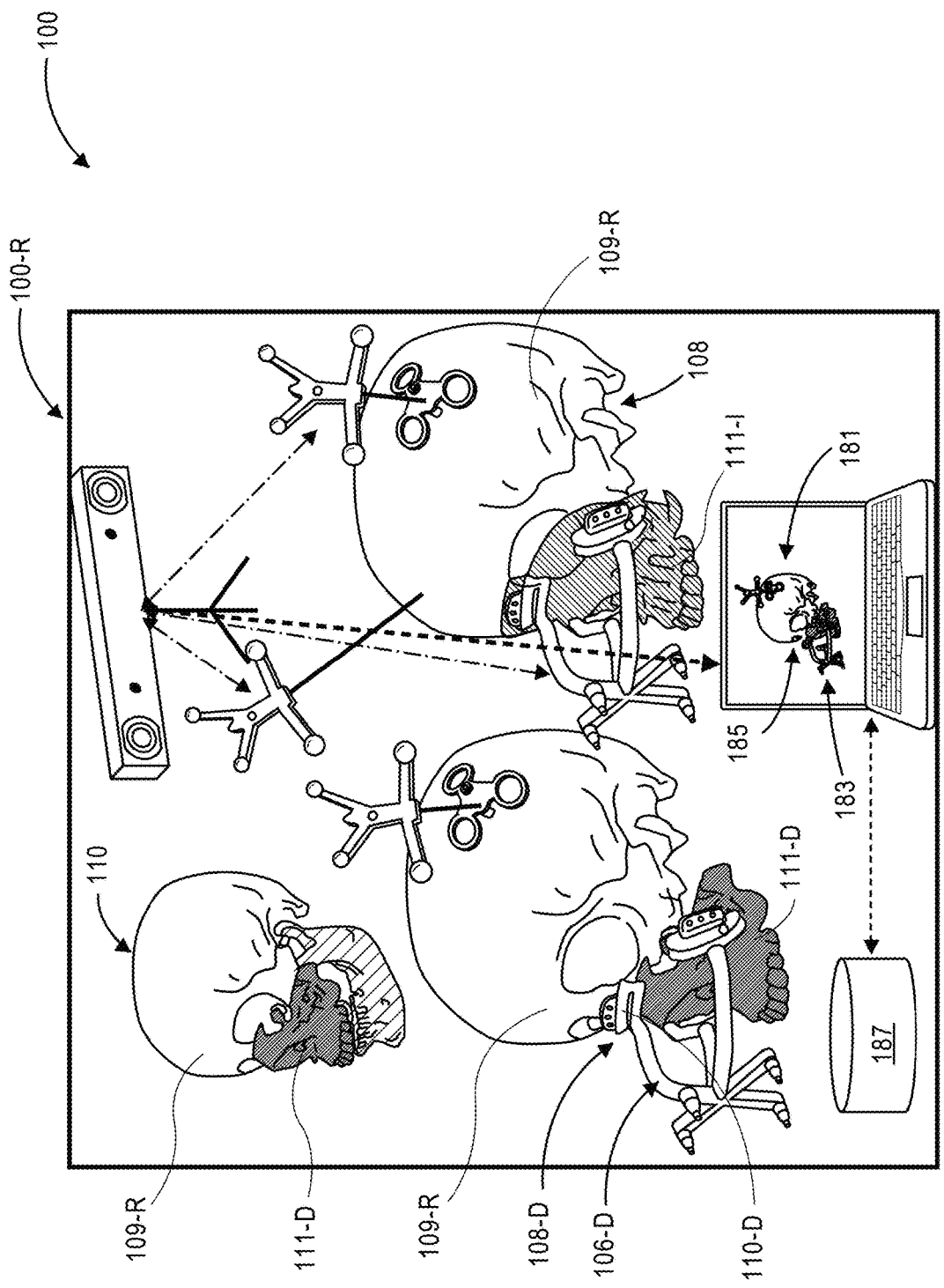
Figure 1B:
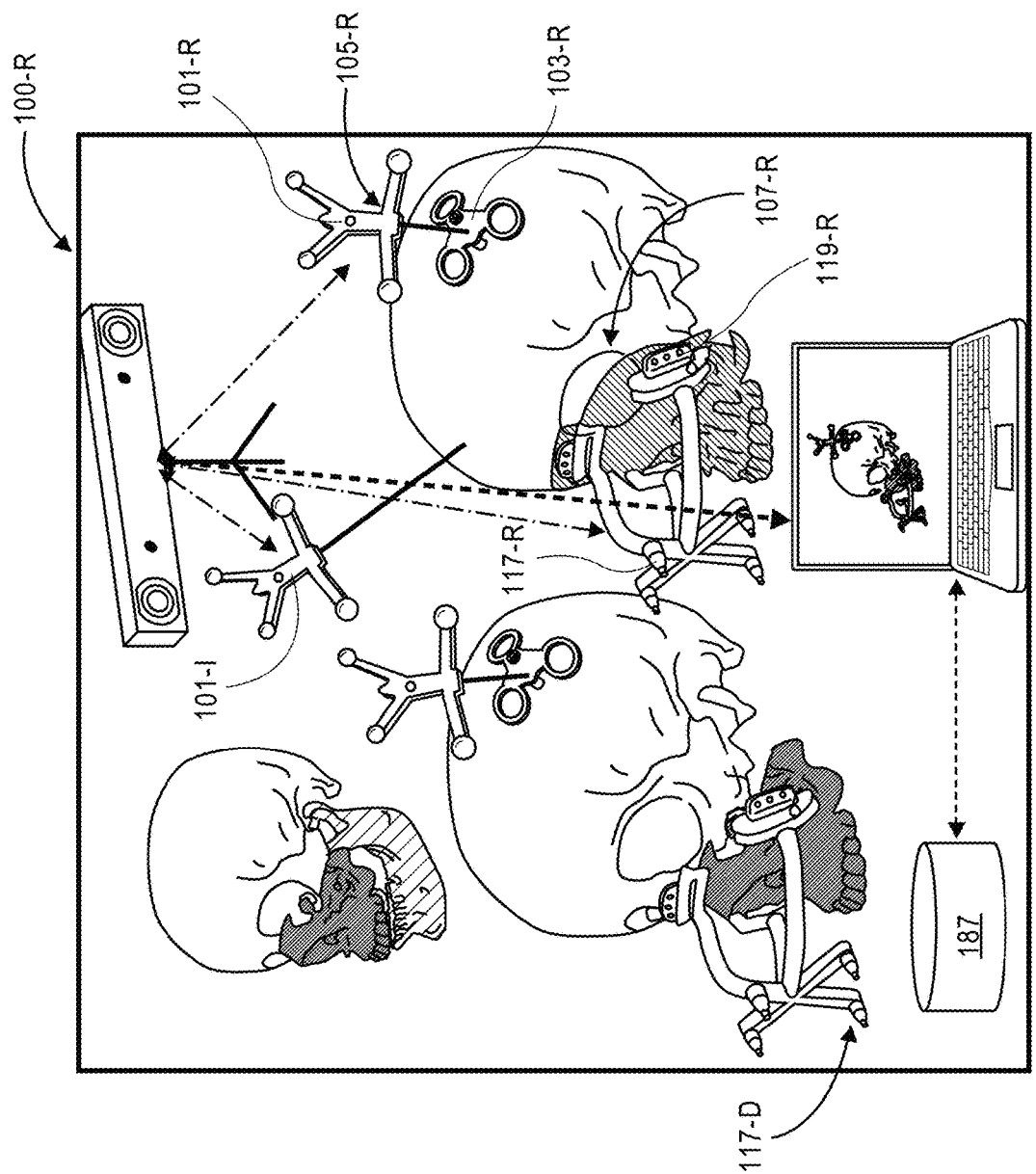

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present embodiments. It is intended that the specification and examples be considered as examples only. The various embodiments are not necessarily mutually exclusive, as some embodiments can be combined with one or more other embodiments to form new embodiments.

In cranioplasty, surgeons remove bone to correct conditions such as a tumor. Preoperative imaging such as CT or magnetic resonance imaging (MRI) identifies the patient anatomy. The surgery is planned using this imaging to identify an area of interest (e.g., the tumor). Bony cuts are created virtually and the implant is designed to fit into the resected region. In single-stage cranioplasty, this implant is ordered oversized to account for additional bone that may be removed during the operation. After resecting the bony region of interest the surgeon shaves down the oversized implant to fit into the resected area. In embodiments described herein, there are methods and devices for reducing the time necessary for reducing the size of an implant for better sizing relative to the removed bone. The methods rely on the use of a computer-assisted surgery system (here, a CAPE system).

A CCI may be either supplied by a third-party vendor, printed with an additive or subtractive manufacturing device, such as a 3D printer, that receives instructions generated provided by a system of the embodiments, as described below, so that a custom implant is available to the surgeon and placed utilizing feedback from the CAPE system to achieve ideal positioning and alignment to the native anatomy. An embodiment of the CAPE system described above can be used to provide the clinician with real-time visual feedback as to the ideal positioning of the implant (i.e. planned versus actual). Also, the CAPE system can access computer-readable reconstructions of a being's anatomy, such as computer-readable files containing soft tissue and/or skeletal CT scan data, which may be uploaded ahead of time into a memory of a computer of the CAPE system, and which can be utilized to by a clinician for predicting a patient's appearance during and after surgery.

At least some embodiments described herein can be used for the immediate surgical repair of large cranial defects (e.g., >5 cm$^2$). For example, embodiments described herein may be used for designing, forming and implanting customized craniofacial implants following benign/malignant skull neoplasm (tumor) resection (i.e., referred to as "single-stage implant cranioplasty").

For example, embodiments provide visualization related to a tumor, the resulting skull defect, and the reshaped implant for exact positioning. In other words, in an embodiment, a CAPE system can be used for improving both the pre-operative planning and intra-operative execution of single-stage implant cranioplasties.

As described above, cranioplasties may be performed to reconstruct large defects following stroke, trauma, aneurysmal bleeding, bone flap removal for infection, and oncological ablation. With this in mind, embodiments described herein include a computer-assisted algorithm that may allow surgeons to reconstruct tumor defects with pre-customized CCIs for an ideal result.

Accordingly, embodiments described herein may be used by surgeons in performing single-stage cranioplasty following oncological resection. In other words, embodiments include algorithms for real-time updates related to single-stage customized implant cranioplasty. For example, in an embodiment, a CAPE system, which is a single, seamless platform capable of being used for both planning (pre-op use) and navigation (intra-op use), overcomes the limitations of conventional systems that do either one or the other. In addition, embodiments include novel hardware such as a rigid cranial reference mount.

A computer-assisted surgical system, such as the system 100 is depicted in FIGS. 1A-1G. System 100 may be utilized, for the pre-operative planning and intra-operative execution of a single-stage implant cranioplasty 100-R instead of (or in addition to) transplantation. For example, in a single-stage implant cranioplasty, a being's anatomy 108, which may be that of a human being, may include an anatomical feature 111-D, such as a diseased portion of the anatomy, that requires removal or replacement with an implant 111-i. During a surgical procedure, the anatomical feature 111-D may be separated from the being 108 by cutting away from healthy portions 109-R of the being's anatomy. For example, a custom-made cutting guide 106-D may be used to provide a surgeon with slots that provide access for a cutting tool at preselecting cutting locations along the being's anatomy. After cutting sufficiently through the being's anatomy at the locations specified by the cutting guide 117-D, the anatomical feature is removed away from the being. Subsequently, an implant, such as a customized craniofacial implant 111-I, which may be fabricated via additive or subtractive manufacturing technology, may be attached near the healthy portions 109-R of the being's anatomy via an attachment 119-R.

System 100 may include a reference unit 105-R, an implant 111-I and a detector 113-R. The reference unit 105-R may include a first trackable element 101-R. The implant may include a second trackable element 101-I. The implant 111-I may include an attachment 119-R which may have a contoured attachment surface 107-R. In addition to, or instead of trackable element 101-R, the attachment 119-R may also include one of a trackable element 117-R. The detector may be configured to provide at least one signal 191 corresponding to a detected location of at least one of the first trackable element 101-R and the trackable element 117-R. Reference unit 105-R may include a cranial reference mount 103-R that may be attached to a first anatomical feature 110 (such as a reference feature of a being's anatomy) to provide a static frame of reference for tracking the location of first trackable element 101-R.

The system 100 may further include a cutting guide 106-D having a third trackable element 117-D, and may be detected by the detector 113-R. Thus, the at least one signal 191 may further correspond to a detected location of at the third trackable element 117-D of the cutting guide 106-D. The cutting guide 106-D may be a surgical guide assembly having an attachment device 108-D configured to be coupled to a bone. A cut location indicator 110-D may be coupled to the attachment device. The cut location indicator identifies a location where the bone is to be cut. The support structure may be configured to have the third trackable element 117-D coupled thereto.

The system 100 may also include at least one computer 115-R, that receives the at least one signal 191 from detector 113-R, may also include an additive manufacturing device 187, which may be in communication with and controlled by the computer 115-R. The computer may be connected to a display on which computer-readable reconstructions of items, such as the implant and a being's anatomy, may be displayed. The at least one signal 191 may be communicated between the detector and computer via a communications link, which may include data transmission wires and/or wireless transmissions either of which may be communicated through a network, such as a local area network (LAN) or wide area network (WAN), including communication over an intranet or over the internet, including TCP/IP data transfer. The at least one computer 115-R may be selected from a desktop computer, a network computer, a mainframe, a server, or a laptop. The at least one computer may be configured to access at least one computer-readable reconstruction of at least one object, such as a being's anatomy, or at least portions of the being's anatomy, for example, a first computer-readable reconstruction 181 and a second computer-readable reconstruction 185, and a third computer-readable reconstruction. The computer-readable reconstruction may include three-dimensional (3D) views, such as those created by scanning a patient via, for example, CT scan. At least one display may be connected to the at least one computer 115-R. The display may be configured to represent the computer-readable reconstruction in a format visible to a user. The first computer may include at least one memory to store data and instructions, and at least one processor configured to access the at least one memory and to execute instructions such as instructions included in software files.

The detector 113-R may be an optical tracker, a magnetic tracker or both an optical tracker and a magnetic tracker. Optical trackers typically emit and capture light in the invisible (infrared) electromagnetic spectrum. Trackable fiducials (i.e., the trackable elements) used with these systems can include passive (i.e., reflective) or active (i.e., those that actively emit infrared light) markers. Using specific geometries known to the camera, the pose of a reference can be tracked through a field of view (as indicated by the dash-dotted lines). An example system is the NDI Polaris available from Northern Digital, Inc. (Ontario, Canada). Magnetic trackers rely on a magnetic field generator and (typically) a passive coil architecture. The field generator creates a time-varying field, which induces a current in the passive sensor. This current is measured and, through a calibration procedure, used to identify up to a 6-dof pose of the sensor. An example system is the NDI Aurora available from Northern Digital, Inc. (Ontario, Canada).

One or more of the first trackable element 101-R, the second trackable element 101-I, and the third trackable element 117-D, may be an infrared (IR) reflector or an IR emitter, each of which may be detachably connected to an attachment surface. As an example, an IR reflector may be a detachably connected surface, such as a sphere. As an example, an IR emitter may be a light emitting diode configured to emit infrared light.

The implant 111-I may be fabricated during a surgical procedure by an additive or subtractive manufacturing device, or may be a pre-fabricated implant such as a $3^{rd}$-party sourced alloplastic implant, including a customized craniofacial implant (CCI) implant. In an embodiment, the implant may include a polymer, metal, bioengineered material, or combinations thereof. For example, the implant may include titanium mesh, porous hydroxyapatite (HA), polymethylmethacrylate (PMMA), polyether ether ketone (PEEK) and/or combinations thereof.

Figure 2:
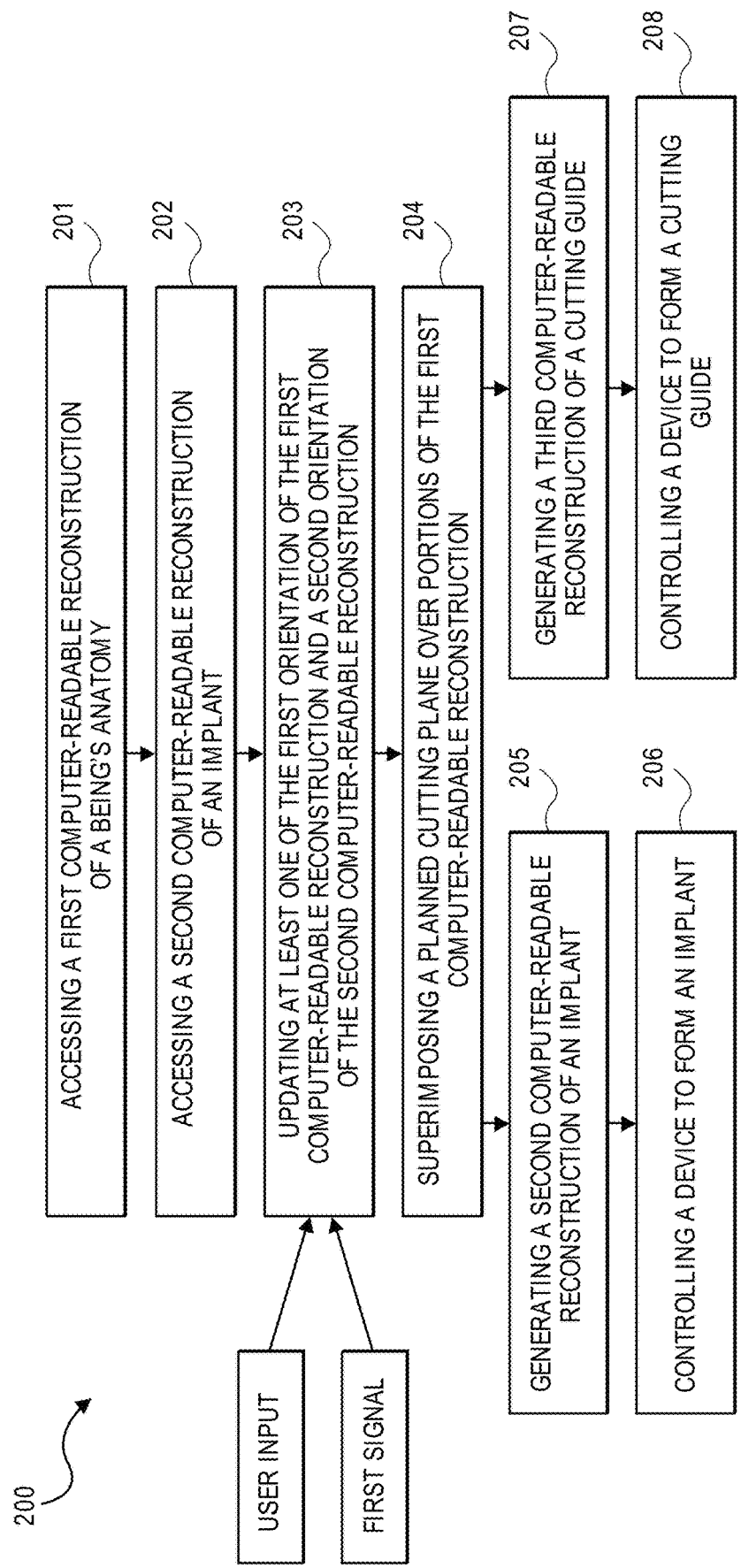
FIG. 2 is a flowchart depicting representative steps for executing a method of an embodiment.

The first computer may include at least one memory to store data and instructions, and at least one processor configured to access the at least one memory and to execute instructions, such as instructions 200 included in the flow chart in FIG. 2. Instructions 200 may include one or more of the steps included in the flowchart on FIG. 2. For purposes of providing examples, some of the steps are described below with reference to components of system 100 from FIGS. 1A-1G.

In an embodiment, instructions 200 include accessing a first computer-readable reconstruction of a being's anatomy at 201 and accessing a second computer-readable reconstruction of an implant at 202. The first computer-readable reconstruction of the being's anatomy may include a first updatable orientation and the second computer-readable reconstruction of the implant may include a second updatable orientation.

During a surgical procedure, such as an implantation of an alloplastic, metal and/or bioengineered implant onto the craniomaxillofacial anatomy of a patient being's anatomy (i.e. head or face), it is useful to track the location of the implant relative to the anatomy of the patient being before, during and/or after the implantation. Accordingly, a signal—such as the at least one signal 191 in the system 100—may correspond to a location of the first, second and/or third trackable element as detected by the detector 113. Thus, the instructions 200 may also include updating the orientation of the first, second and/or third computer-readable reconstruction of the implant with an orientation that is updated based on the signal, which may correspond to a physical location of the first, second and/or third trackable element, respectively, as sensed by the detector. For example, at 203, the instructions 200 may also include updating at least one of the first (updatable) orientation and the second (updatable) orientation. In an example, step 203 may be initiated by user input, for example, via user interaction with the computer, or by a signal, such as a signal provided by a detector. As described above, the first orientation and the second orientation may be updated, for example, on a display connected to the computer, in response to the at least one signal.

The instructions 200 may include superimposing a planned cutting plane over portions of the first computer-readable reconstruction at 204. Other steps may include generating a second computer-readable reconstruction of an implant at 205 and controlling an additive manufacturing device at 206 to form an implant. In an example, the second computer-readable reconstruction of the implant generated at 205 may include a geometry defined by at least one of: i) an interface between the planned cutting plane and the first computer-readable reconstruction, and ii) a selected portion of the computer-readable reconstruction, the selected portion comprising an anatomical feature of the being's anatomy, including but not limited to oncological defect sites, such as a benign/malignant skull neoplasm, large defects following stroke, trauma, aneurysmal bleeding, bone flap removal for infection, and oncological ablation. Additionally, the implant fabricated by the manufacturing device at 206 may have dimensions defined by the geometry of the second computer-readable reconstruction.

The instructions 200 may also include generating a third computer-readable reconstruction of a cutting guide at 207 and controlling the additive manufacturing device to form a cutting guide at 208. In an example, the third computer-readable reconstruction of the cutting guide may include a geometry defined by an interface between the planned cutting plane and the first computer-readable reconstruction, and may also include a third updatable orientation. Additionally, the cutting guide fabricated by the manufacturing device at 208 may include selected dimensions of the geometry of the third computer-readable reconstruction.

The device may be any manufacturing device that fabricates an object based on instructions, such as computer-readable instructions, for example, instructions provided in digital data, including any device that utilizes additive or subtractive manufacturing technologies, such as those that fabricate an object from appropriately approved materials for medical use. Accordingly, the at least one device may be an additive manufacturing device, such as a 3D printer, or another kind of manufacturing device, including subtractive manufacturing device, such as a Computer Numerical Control (CNC) machine. Examples of additive manufacturing technologies may include vat polymerization (e.g., PROJET® 6000, 7000, 8000 available from 3D Systems Corp., Rock Hill, SC), materials jetting (e.g., Objet500 or Eden250, each available from Stratasys, Ltd., Eden Prairie, MN), powder binding (e.g., PROJET® 460, 650 available from 3D Systems Corp., Rock Hill, SC), powder fusion (e.g., EBM® available from Arcam AB, Sweden), material extrusion (e.g., Fortus250 or Fortus400, available from Stratasys, Ltd., Eden Prairie, MN), or any one denoted by the ASTM F42 committee on additive manufacturing. Accordingly, system 100 may include a device (not shown) for manufacturing components, such as cutting guides, reference units and/or the trackable elements, and the device may be connected to the at least one first computer via the communications link described above. The instructions may also include generating a computer-readable file that contains instructions for manufacturing the cutting guide and/or implant, for example a computer-readable file that contains dimensions of a component, such as a cutting guide based on the geometry of the third computer-readable reconstruction. The computer-readable reconstruction of the being's anatomy may be a computer-readable file created from a CT-scan. For example, the computer-readable reconstruction may be a 3D reconstruction of a patient's anatomy.

In an embodiment, there is also a computer-assisted surgical method. The method includes use of the CAPE system, which may provide a user enhanced implant reconstruction experience, for example, providing a surgeon unprecedented, immediate visual feedback and allowing single-stage implant cranioplasty and all related craniomaxillofacial reconstruction for scenarios related to skull neoplasms, etc—in situations where the tumor defect is not known beforehand, but where a customized implant is needed requiring on-table modification via CAPE system guidance.

Generally, the method can include the following: a) generating and/or accessing a computer-readable reconstruction of a patient's anatomy, such as via a preoperative CT scan that includes an anatomical feature, such as a defect, and constructing a 3D model of the anatomy; b) preselecting a resection area on the model; c) determining implant dimensions (can be a few millimeters greater than the size of the defect) and fabricating the implant with an additive and/or subtractive manufacturing device incorporated with the CAPE system; d) designing a trackable cutting guide based on the 3D model and fabricate with an additive and/or subtractive manufacturing device incorporated with the CAPE system; e) attaching a reference unit having a trackable element onto the patient's anatomy, such as at the patient's skull; f) registering the location of the trackable element/reference unit to the computer-readable reconstruction (preoperative CT scan); g) using the optically trackable cutting guide to perform bone cuts in the patient; h) using a detector to generate a signal in response to performing a trace of the defect boundaries, for example, if additional resection is required; i) superimposing information corresponding to signals generated by optical digitizer, such as signals in response to performing a trace of the defect boundaries, on the computer-readable reconstruction; j) registering the implant to the computer-readable reconstruction with the optical digitizer, for example, via tracking a location of a trackable element attached to the implant; k) tracing cut lines on the implant based on information obtained from the 3D model, such as a size mismatch between the implant and the defect; l) attaching the implant to the patient; m) obtaining a post-operative image of the patient and the attached implant, such as a CT scan.

The method may include any step or combination of steps included in the flow charts of FIG. 3-4 and described below. In an example shown in the flow-chart of FIG. 3, with reference to the features of the system 100 in FIGS. 1A-1H, a method 300 can include attaching a reference unit that includes a first trackable element to a first anatomical feature of a being's anatomy at 301. The method may also include detecting a location of at least the first trackable element with a detector at 302, and accessing a first computer-readable reconstruction of the being's anatomy at 303. The detector may be detector 113 as described above, and may be configured to provide at least one signal corresponding to a detected location of at least the first trackable element. The first computer-readable reconstruction may be first computer-readable reconstruction 181 and may include a first updatable orientation. Accordingly, the first updatable orientation may be updated in response to user input and/or the at least one signal such as the at least one signal 191 described above.

Figure 3:
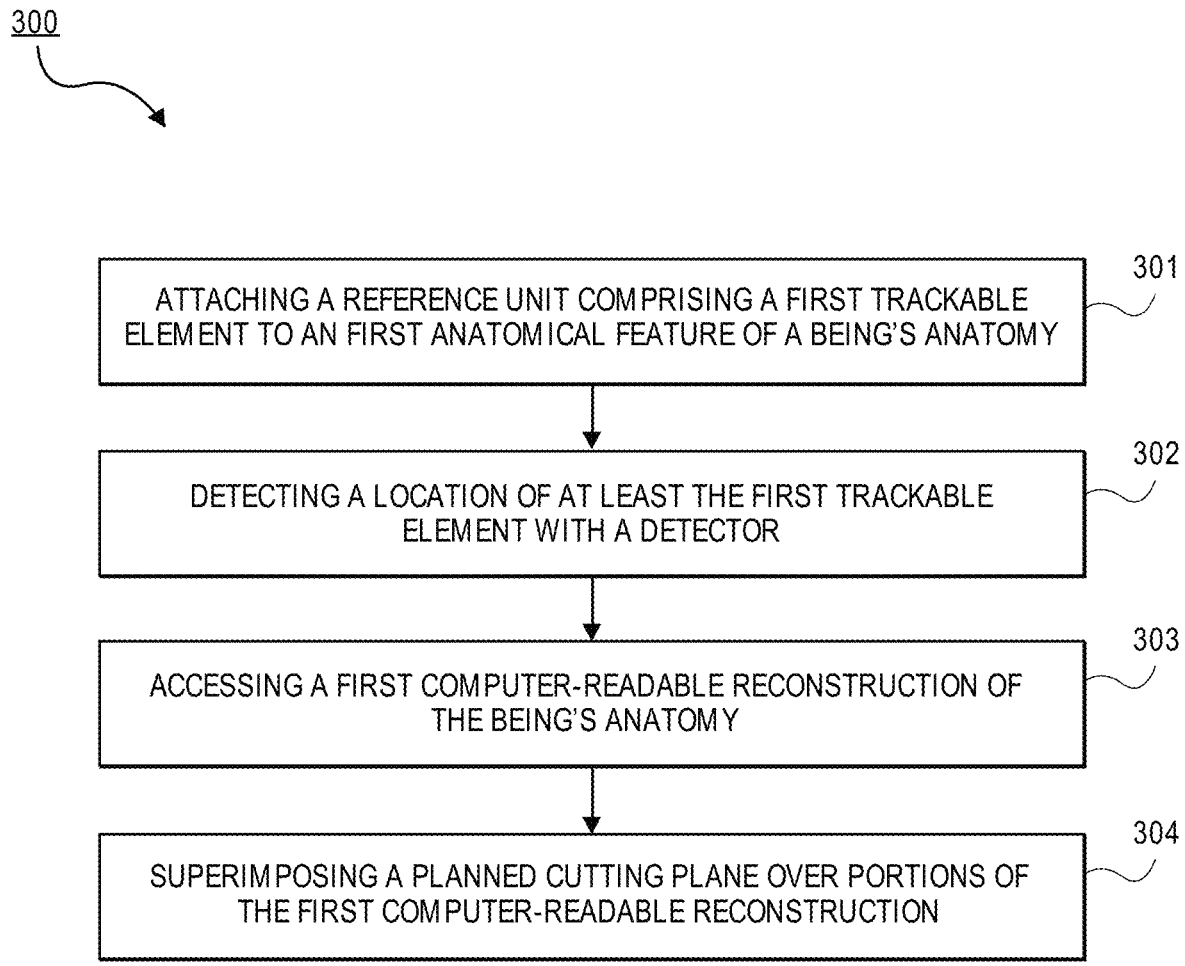
FIG. 3 is a flowcharts depicting representative steps for executing a method of an embodiment.
Figure 4:
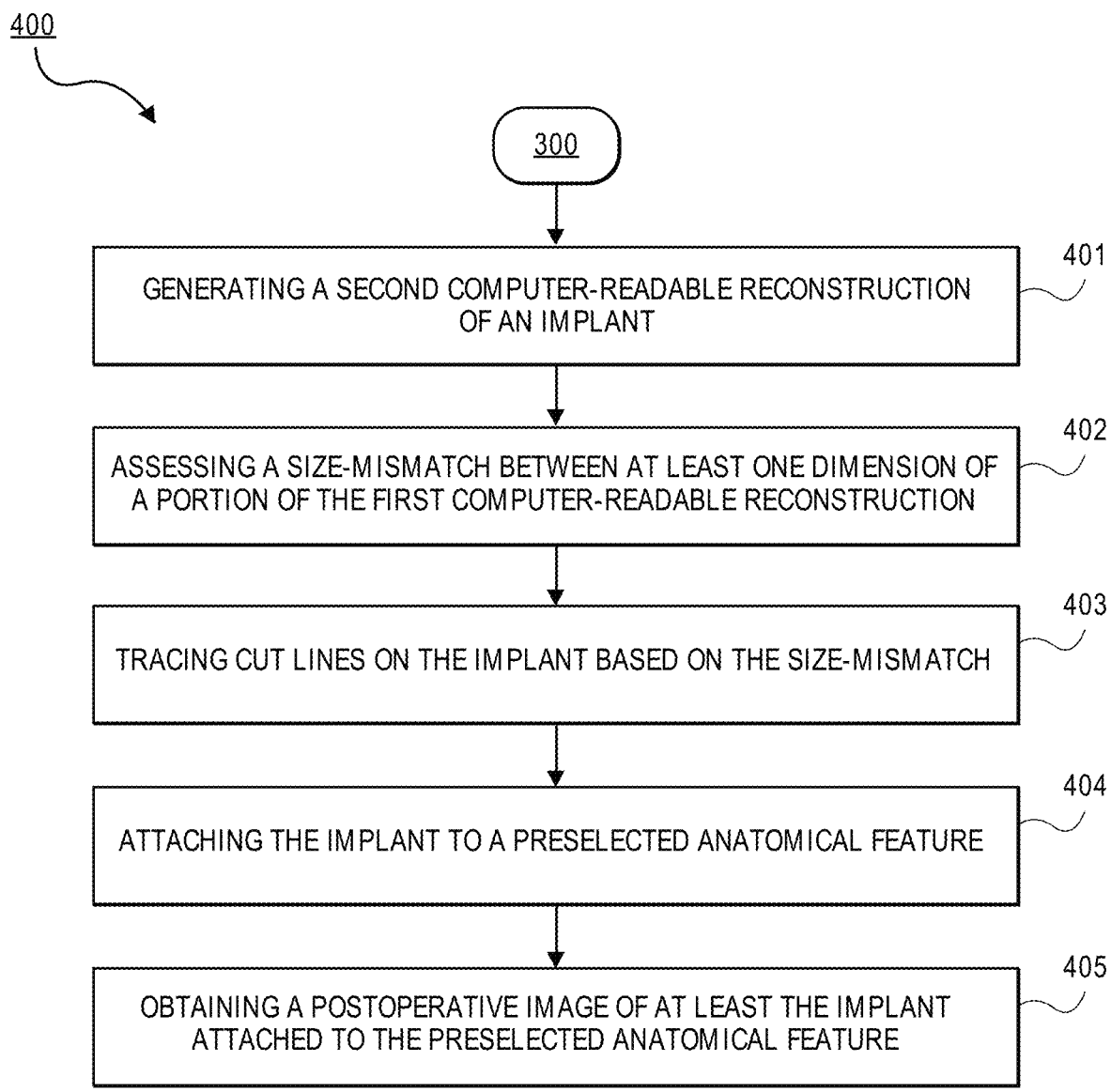
FIG. 4 is a flowchart depicting representative steps for executing a method of an embodiment.
Figure 5:
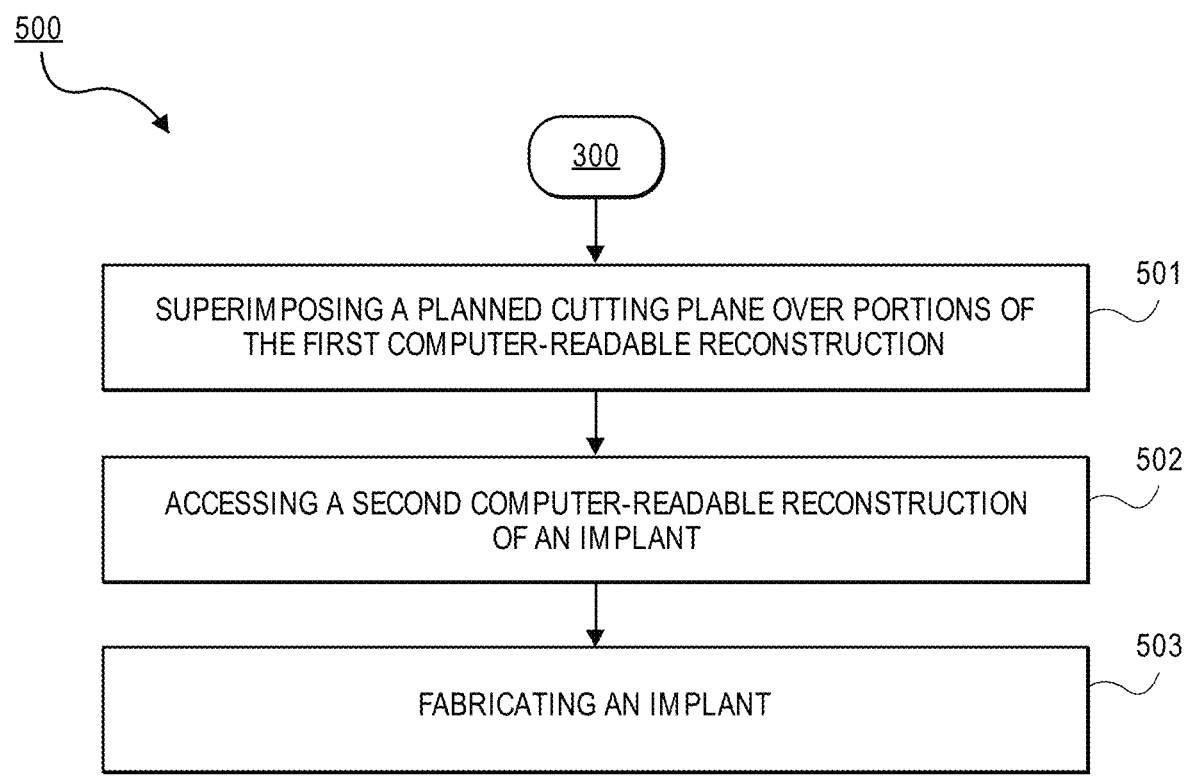
FIG. 5 is a flowchart depicting representative steps for executing a method of an embodiment.

In an embodiment, a method 400 may include one or more or all of the steps of method 300 of FIG. 3 and may also include any step or combination of steps included in the flow charts of FIGS. 3-5. In an example shown in the flow chart of FIG. 4, in addition to method 300, method 400 may include generating a second computer-readable reconstruction of an implant at 401. The second computer-readable reconstruction may be second computer-readable reconstruction 185 as described above, and may include a second updatable orientation, such as an orientation that may be updated in response to user input and/or the at least one signal, such as the at least one signal 191 described above. The method 400 may also include assessing a size-mismatch between at least one dimension of a portion of the first computer-readable reconstruction, for example, a portion corresponding to a selected anatomical feature of the being's anatomy, and at least one dimension of the second computer-readable reconstruction at 402. In an example, assessment of the size-mismatch may be performed via a cephalometric analysis, including a real-time cephalometric analysis. The method 400 may also include tracing cut lines on the implant based on the size-mismatch. In an example, the cut lines may be traced on the implant such that an anatomical discrepancy at an area of removal or reconstruction of the anatomical feature is minimized. In an example, the anatomical discrepancy may be minimized based on a preselected tolerance, for example, in instructions provided for fabricating the implant, including instructions provided in computer-readable files, such as digital data, provided to an implant manufacturing device. The method 400 may also include attaching the implant to a preselected anatomical feature at 404, such as to a patients anatomy surrounding oncological defect sites, such as a benign/malignant skeletal neoplasm, or large defect sites formed following stroke, trauma, aneurysmal bleeding, bone flap removal for infection, and oncological ablation. After implantation of the implant at 404, for example, the method can also include obtaining a post operative image of at least the implant attached to the preselected anatomical feature at 405. For example, a CT scan may be taken of the patient with implant attached.

In an embodiment, a method 500 may include one or more or all of the steps of method 300 in FIG. 3, and may also include any step or combination of steps included in the flow charts of FIGS. 3-5. In an example shown in the flowchart in FIG. 5, in addition to method 300, method 500 may include superimposing a planned cutting plane over portions of the first computer-readable reconstruction at 501. In an example, the planned cutting plane may be superimposed to bisect the first computer-readable reconstruction to define at least one portion of the first-computer-readable reconstruction corresponding to at least one diseased anatomical feature of the being's anatomy that is to be removed or replaced. Accordingly, the planned cutting plane may be planned cutting plane as described above, and the first computer-readable reconstruction may be the first computer-readable reconstruction 181 as described above. The method 500 may also include accessing a second computer-readable reconstruction of an implant at 502 and fabricating an implant at 503. The second computer-readable reconstruction may be second computer-readable reconstruction 185 as described above, and may include a second updatable orientation, such as an orientation that may be updated in response to user input and/or the at least one signal, such as the at least one signal 191 described above. The implant may be implant 111-I described above, and may include dimensions that correspond to the geometry of the second computer-readable reconstruction. Additionally, a second trackable element may be provided on the implant. For example, a second trackable element such as trackable element 101-I as described above, may be may be incorporated in the design of the implant as a detachably connected trackable element, or may be formed separate from the implant and attached to the implant. It is noted that the at least one signal, such as the at least one signal 191, may also correspond to a detected location of the second trackable element, such as that detected by detector 113. It is also noted that the planned cutting plane may also include a fourth updatable orientation, such as an orientation that may be updated in response to user input.

The described method may be utilized during a surgical procedure, such as a surgical implantation procedure for various forms of craniomaxillofacial surgery including an implant-based cranioplasty. The implant may be a custom, 3D craniofacial implant made of either alloplastic materials or biologic tissue engineered cells as described above for implant 111-I and a being, such as a recipient being, on whom the surgical procedure is performed.

During a surgical procedure, such as an implantation of an alloplastic, metal and/or bioengineered implant onto the anatomy of a patient, it is useful to track the location of the implant relative to the anatomy of the patient before, during and/or after the implantation. Accordingly, the signal—such as the at least one signal 191 in the system 100—may correspond to a location of the first, second and/or third trackable element as detected by the detector 113. Thus, the computer-assisted surgical method of the embodiments may include updating the orientation of the first, second and/or third computer-readable reconstruction of the implant with an orientation that is updated based on the signal, which may correspond to a physical location of the first, second and/or third trackable element, respectively, as sensed by the detector.

In an example, the CAPE surgical system of the embodiments as described herein can be utilized by a user, such as a surgeon, to quickly and accurately shave down an oversized CCI. Such an oversized CCI may be designed to the curvature specific only to the patient's skull—using information about the intraoperative bony resection following instantaneous, computer-assisted registration. In an embodiment of a surgical method described with reference to FIGS. 6-9, a clinician (for example, a surgeon) digitizes points of the removed anatomical feature, such as a cut region from which bone is removed to correct conditions such as a tumor, and the anatomical defect is assessed in real-time using the CAPE system. In other words, a computer of the system accesses first computer-readable reconstruction of a being's anatomy, which may be preoperative surface models of the skull (e.g., segmented from CT). Additionally, a computer of the system may access a second computer-readable reconstruction of an implant, which may be a surface model of the oversized pre-fabricated CCI.

Figure 6A:
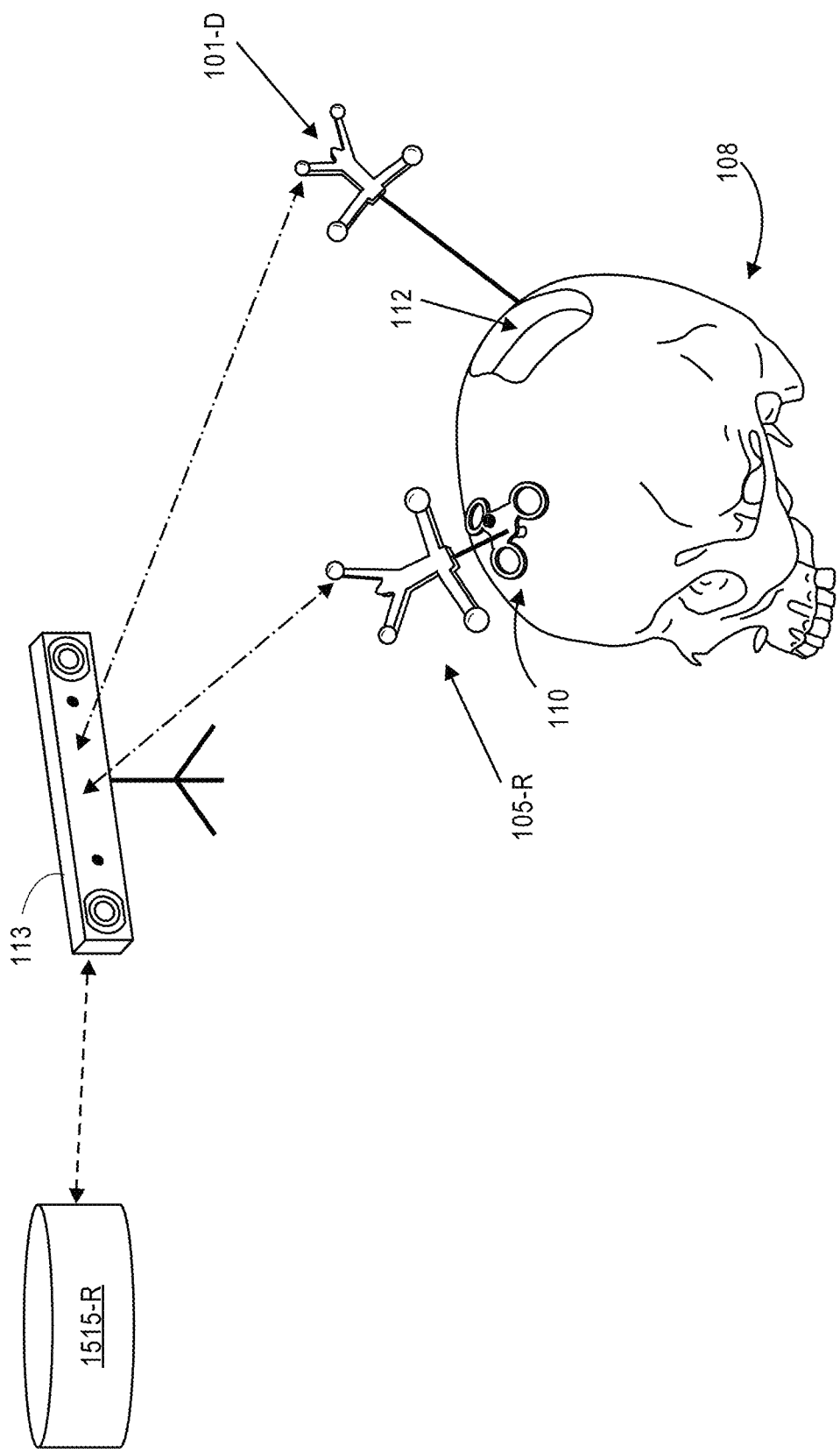
FIG. 6A illustrates an example tracker digitization. A reference geometry is attached to the patient (via a cranial mount, for example) and to a digitizer. A tracking unit, such as an optical tracker, tracks the reference geometries. The digitizer captures the outline of the cut region.
Figure 6B:
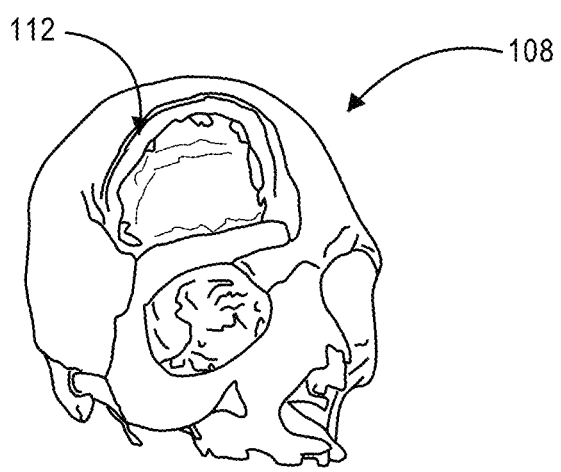
FIG. 6B illustrates a three dimensional rendering formed according to a computer-readable reconstruction of a being's anatomy including a representation of a cranial defect as captured using the system of FIG. 6A.
Figure 6C:
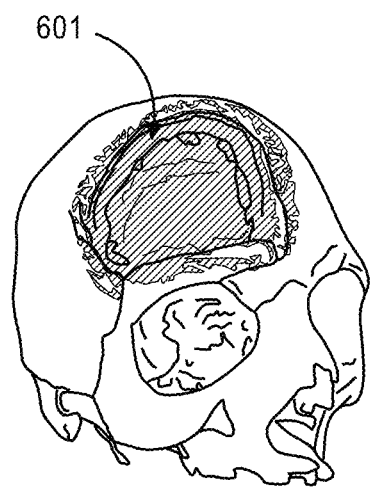
FIG. 6C illustrates the three dimensional rendering of FIG. 6B and includes an implant overlay for use in performing a computer-assisted cranioplasty in accordance to an embodiment. The implant overall is a computer-readable representation of a geometry defining the dimensions of a resized implant and may be superimposed over the three dimensional rendering.
Figure 6D:
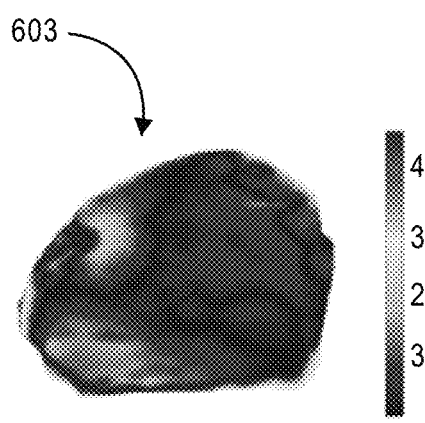
FIG. 6D is a distance map generated from a quantitative analysis between dimensions of the implant and dimensions of a defect site on a being's anatomy.

As illustrated in FIGS. 6A-6D, digitization can be achieved through tracking technology such as an optical (infrared) and/or electromagnetic trackers (detector 113) as in system 100. A trackable pointer tool 101-D with a digitizer (a trackable element) and/or a reference unit 105-R can be tracked by the detector 113. As described previously, the tracker may be a detector that generates signals in response to sensing a trackable element of the trackable pointer tool 101-D and/or of reference unit 105-R. The trackable pointer tool 101-D can be used for tracing a geometry of the area of interest 112, the geometry being digitized and converted into a computer-readable pattern such as a trace. For example, as shown in FIG. 6B, by using a registration between the patient anatomy and patient model (i.e., a computer-readable reconstruction of the patient's anatomy) such as via a location of a static point provided by reference element 105-R, the points from the digitized trace of the area of interest 112 can be transformed to a patient model such as the computer-readable representation of the being's anatomy 108. In other words, as the clinician traces the geometry of the area of interest 112, the detector 113 detects an orientation and location of the trackable pointer tool 101-D relative to a location of the reference unit 105-R, generates signals corresponding to the sensed location of the trackable pointer tool 101-D and/or reference unit 105-R and sends those signals to a computer which, in turn, generates a computer-readable reconstruction of the geometry which can be superimposed over a computer-readable reconstruction of the patient's anatomy. As shown in FIG. 6C, a computer-readable representation 601 of the geometry of a pre-fabricated implant may be superimposed over the computer-readable representation of the being's anatomy 108 to show offset in sizing. In some instances, the pre-fabricated implant's dimensions, for example, thickness, may not match the skull thickness. Accordingly, a distance map 603 shown in FIG. 6D may be generated to show similarities/differences between the implants and defects by identifying the closest point on the implant for each vertex of a corresponding defect surface.

Accordingly, a surgical method can include attaching a reference unit 105-R having a first trackable element to a first anatomical feature 110 of a being's anatomy 108; detecting a location of at least the first trackable element with a detector 113 configured to generate at least one first signal corresponding to a detected location of at least the first trackable element, the generated signal being provided to, for example, a computer 115-R having a memory and a processor for executing instructions. The method may include accessing a first computer-readable reconstruction of the being's anatomy, the first computer-readable reconstruction comprising a first updatable orientation, wherein the first updatable orientation is updated in response to the at least one first signal. The method can also include accessing a second computer-readable reconstruction of an implant, the second computer-readable reconstruction comprising a second updatable orientation. The method may also include detecting a location of at least one second trackable element of, for example, the trackable pointer tool 101-D with the detector 113. The detector may further be configured to generate at least one second signal corresponding to a detected location of at least the second trackable element of the trackable pointer tool 101-D, the second generated signal being provided to, for example, computer 115-R. Thus, the method may also include generating at least one updatable, computer-readable trace, the trace corresponding to a geometry based on updated location data for the at least one second trackable element of the trackable pointer tool 101-D. The method also includes superimposing the least one updatable, computer-readable trace over portions of the second computer-readable reconstruction of the implant. In an example, a location of the superimposed computer-readable trace may be manipulated based on user input.

Figure 7:
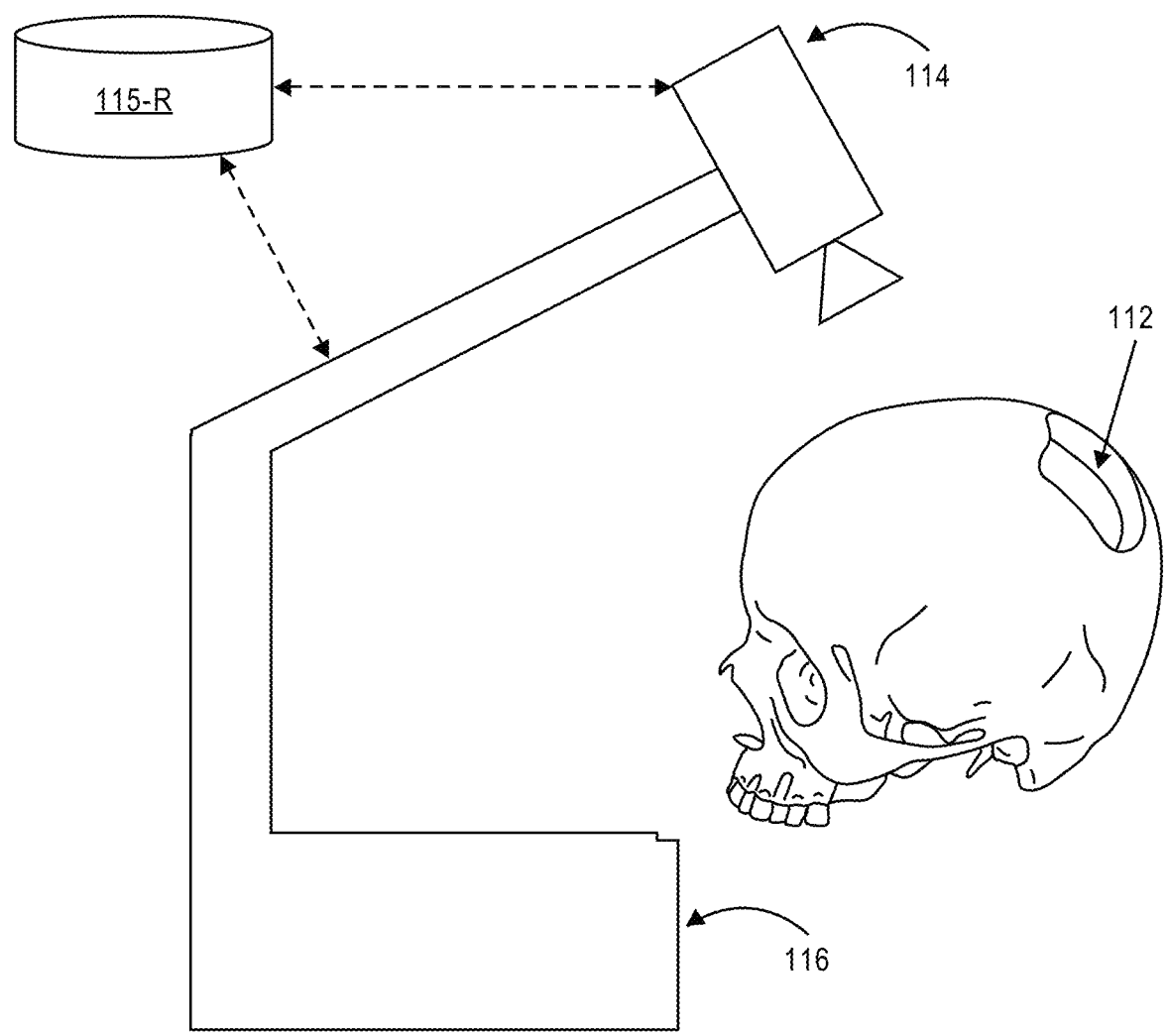
FIG. 7 illustrates an example for camera digitization. The camera can be any of a standard color (RGB) camera, a depth sensor, or a combination of RGB and depth (like the Structure sensor, available from XRPro, LLC (Structure) of Boulder, CO, USA see the web page structure.io/). The camera is attached to a passive arm of a stand. The surgeon uses the camera to take several pictures of a cut region (i.e., a geometry of a patient's anatomical defect). Each time a picture is taken, the camera position is recorded. This information may be stitched into a 3D model from which an outline of the cut region may be extracted.

In another embodiment illustrated in FIG. 7, a computer-readable reconstruction of the area of interest 112, which may be a removed anatomical feature, and/or of other portions of a being's anatomy may be captured via the use of a source 114 for generating the computer-readable reconstruction. The computer-readable reconstruction may be at least one digital image which may be provided to or accessed by computer 115-R. The source 114 may be attached to a passive stand and arm arrangement 116, for example an arrangement that includes encoders, so that it is configured to relay positional information, such as a relative position to a known reference point and tie the positional information with the at least one digital image based on an orientation of the source when such digital image(s) is capture. While in one embodiment, a camera may be attached to the passive arm such as in FIG. 7, any source for generating a computer-readable reconstruction of subject being imaged may be used. Accordingly, the source 114 may be a camera which can be any of a standard color (RGB) camera. The source 114 may also be a depth sensor. The source 114 may also be a laser scanning device. In an embodiment, the source for generating the computer-readable reconstruction of a subject, for example, a removed anatomical feature and/or other portions of a being's anatomy may be any combination of devices that are capable of generating computer-readable reconstructions of the subject of interest. Accordingly, such a combination may include an RGB camera and a depth sensor, for example the Structure sensor, available from Occipital, Inc., of San Francisco, CA). The combination may also include a laser scanning device. In one embodiment, the source is a camera attached the arm and the camera/arm may be moved to at least one position from which an image of the subject of interest is taken. In an embodiment, a computer-readable reconstruction of the subject of interest, (an anatomical feature in FIG. 7) may be generated and may be combined with positional information relative to the base of the arm. The computer-readable reconstruction, i.e., each of the at least one picture/image/digital image, may be stitched together using appropriate software, and may then be registered to the patient/implant, and the region of interest (for example a portion of the anatomical feature, or a geometry of the anatomical feature such as a perimeter of a removed portion of bone) is projected onto the implant. Accordingly, the process of modifying the craniofacial implant for single-stage cranioplasty (by following the projected geometry on the implant, for example, removing portions of the implant according to the projected geometry) can be dramatically reduced, thus decreasing total operative time, limiting blood loss/morbidity, and improving final outcomes.

Once registered, the patient's resected anatomy is digitized and projected onto the CCI. The surgeon traces the resection with a marking tool and shaves the implant to a precise fit on the patient. For example, as shown in FIGS. 8A-9D, after tracing the area of interest, such as a cut-region (i.e., an area of the anatomy featuring the removed anatomical feature) and/or other portions of a being's anatomy as illustrated in FIG. 6, or after creating an image of the cut-region and/or other portions of a being's anatomy via the use of a camera-based images (e.g., digital images) and positional information, as described above for FIG. 7, a visualization routine may be executed by computer 115-R. The visualization routine may be software instructions executed by the computer to generate a display of the computer-readable reconstruction of the cut-region geometry over an oversized CCI.

Figure 8A:
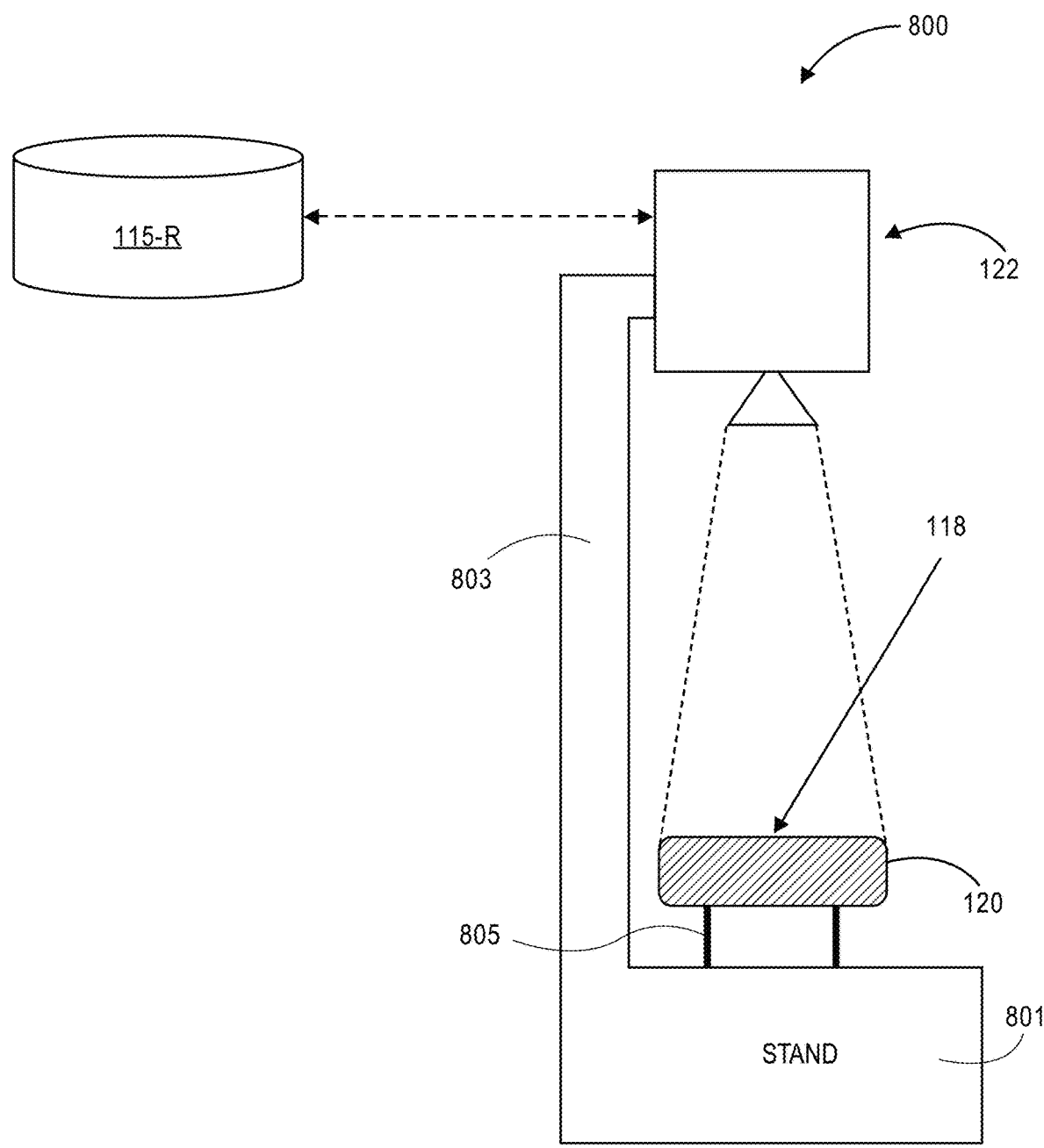
FIG. 8A illustrates an example setup that may be a part of a surgical system for projecting a trace onto the implant according to an embodiment. The setup includes a stand on which the implant is placed and a projector, which may be connected to the stand, for projecting a trace/image onto the implant.
Figure 8B:
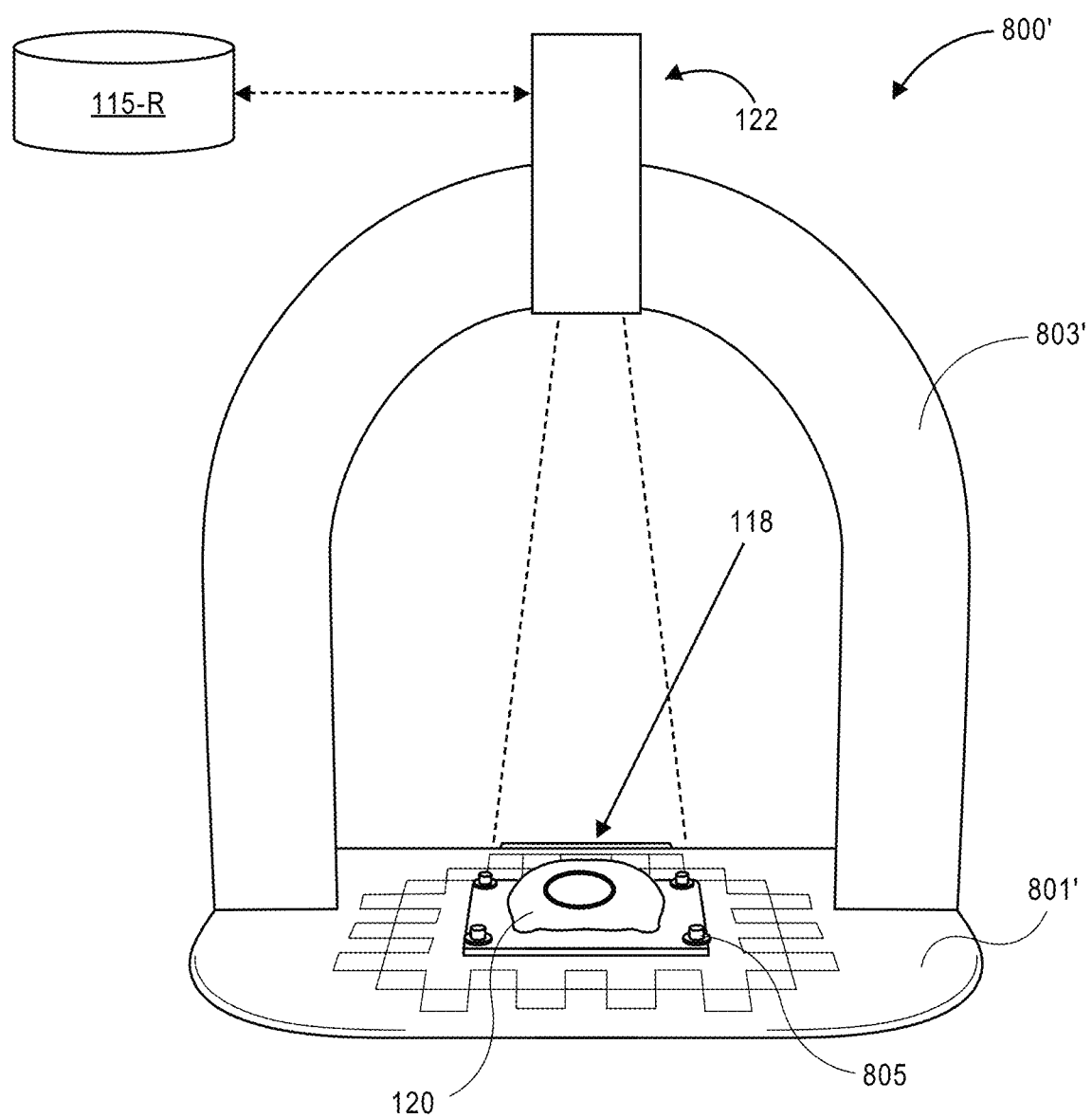
FIG. 8B illustrates an alternative example setup that may be a part of a surgical system for projecting a trace onto an implant according to an embodiment The setup includes a stand on which the implant is placed and a projector, which may be connected to the stand, for projecting a trace/image onto the implant.

In one embodiment as shown in FIG. 8A, a first arrangement 800 for executing a visualization routine is shown. A projector 122 disposed on a stand 801 projects an image onto a surface of an implant 120 from a pre-determined distance h defined by a height of an arm 803. The image may be a virtual reconstruction 118 based on a computer-readable reconstruction of the area of interest 112 of the being's anatomy 108 as described above. That is, the virtual reconstruction 118 is generated from a computer-readable reconstruction of the area of interest that is created as discussed above, onto the implant 120 itself (e.g., an oversized implant). An alternative embodiment shown in FIG. 8B provides an arching stand 801' which may be attached to an operating room table. In an embodiment, a projector 122 disposed on a stand 801' displays an image onto a surface of an implant 120 from a pre-determined distance h defined by a height of arches 803'. The image may be a virtual reconstruction 118 based on a computer-readable reconstruction of the area of interest 112 of the being's anatomy 108 as described above. For both FIGS. 8A-8B, the stands 801 and 801' may be attached to, for example, an operating table. The stands 801, 801' may include sterile surfaces. Additionally, for both FIGS. 8A-8B, the height from which the virtual reconstruction is projected is known, and a thickness or height of the implant is known, the projected virtual reconstruction can be provided to-scale at substantially the dimensions of an anatomical feature of interest as constructed according to the tracking method described above.

Figure 9B:
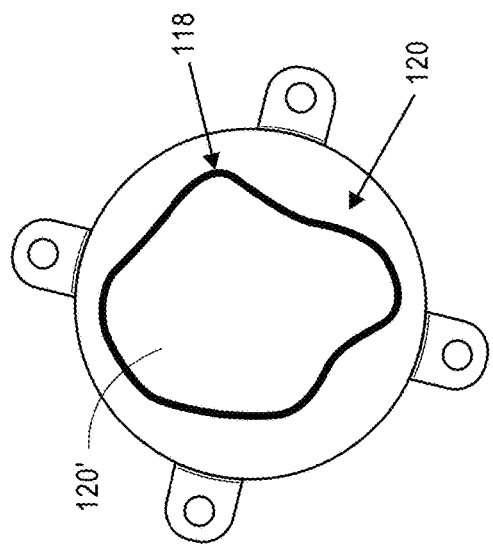
FIGS. 9A-9D illustrates an example surgical method according to an embodiment.
Figure 9D:
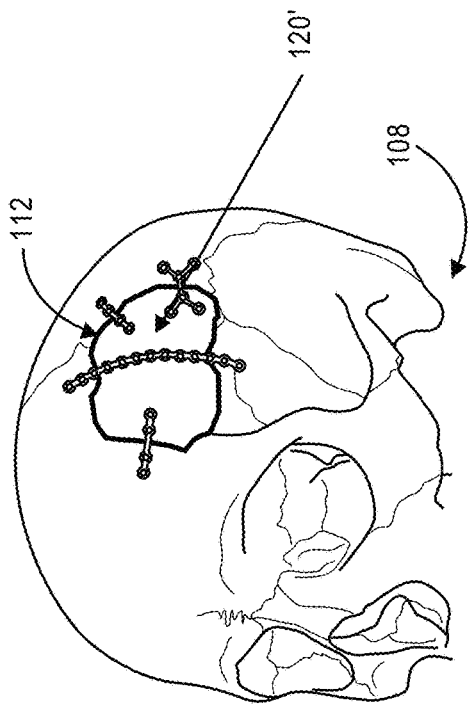
Figure 9A:
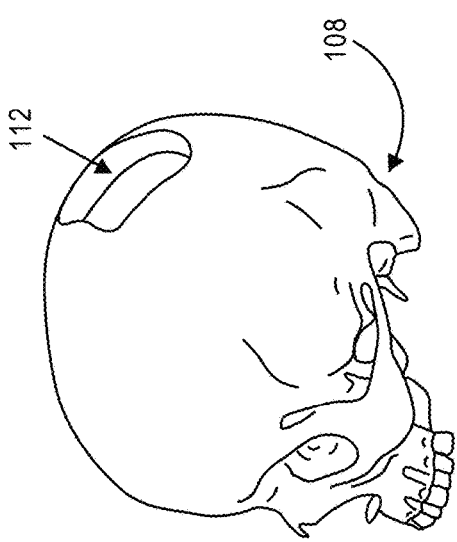
Figure 9C:
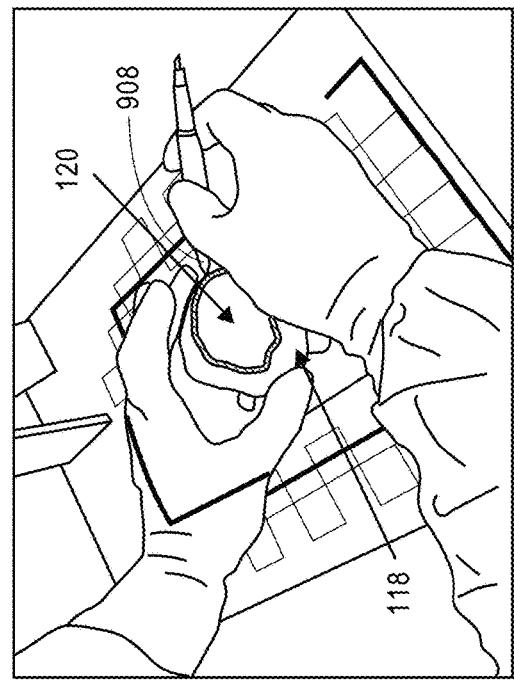

FIGS. 9A-9D illustrates an example surgical method according to an embodiment. In FIG. 9A, an anatomical feature of interest (e.g., a defect) is identified. In an embodiment, the virtual reconstruction 118 of the area of interest 112 may simply be a trace that appears as colored lines 118' projected on the implant as shown in FIG. 9B (which is a top view looking down in, for example, FIG. 8B from the projector 122 onto the implant 120). In an embodiment, the virtual reconstruction 118 of the area of interest may simply be a projected image of the patient's anatomical feature (e.g., to scale) that the clinician can then use to trace around with a marking pen 908 directly on the implant as shown in FIG. 9C. In another embodiment, a virtual reconstruction of the oversized implant (i.e., a computer-readable reconstruction of the oversized implant) can be generated and accessed by the CAPE system computer. A virtual implant generated by the projector 122 and the physical implant may be aligned by changing source 114 parameters (e.g., the model transformation) until the virtual model exactly overlays the physical model. A surgeon may then use a marking tool (e.g., sterile marking pen) to outline the projected points (the trace from the anatomical feature of interest). The surgeon then cuts excess material off of the CCI, for example along the outline of the projected points, and fits the implant into exact place on the patient as shown in FIG. 9D—in a less time-intense, labor-intense manner. Significant time reduction (by up to 90%) and improved implant-to-defect positioning (i.e., fewer gaps between implant and surrounding bone) are both advantages of at least one embodiment.

Figure 10:
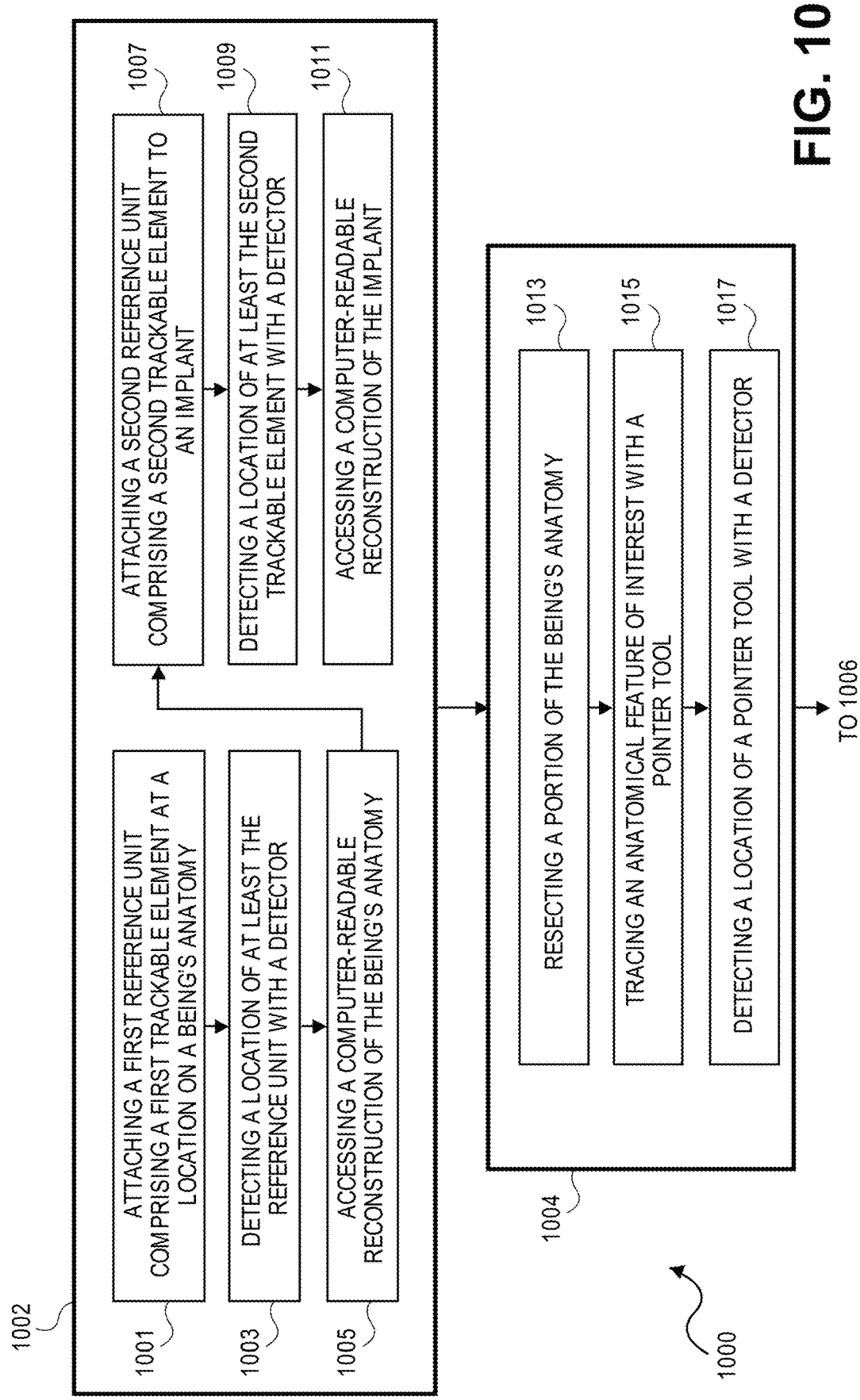
FIG. 10 is a flow chart depicting an embodiment of a surgical method which can be executed for sizing an implant to an anatomical feature.

The methods, tools and systems described with respect to, for example, FIGS. 7-9 may be included in a surgical method, such as surgical method 1000 of FIG. 10 which can be executed for sizing an implant to an anatomical feature. Surgical method 1000 may include one or more of a registration 1002, a surgical procedure 1004, an implant modification 1006 and an implant attachment 1008. For example, the surgical method 1000 may include registration 1002 which includes one or more of attaching a first reference unit comprising a first trackable element at a location on a being's anatomy at 1001, detecting a location of at least the reference unit with a detector at 1003, accessing a computer-readable reconstruction of the being's anatomy 1005, attaching a second reference unit comprising a second trackable element to an implant at 1007, detecting a location of at least the second trackable element with a detector at 1009 and accessing a computer-readable reconstruction of the implant at 1011. The surgical method 1000 may include surgical procedure 1004 which includes one or more of resecting a portion of the beings anatomy at 1013, tracing an anatomical feature of interest with a pointer tool at 1015 and detecting a location of the pointer tool with a detector at 1017. The surgical method 1000 may include an implant modification 1006 which includes one or more of accessing a computer-readable reconstruction of a trace at 1019, superimposing the computer-readable reconstruction of the trace on the computer-readable reconstruction of the implant at 1021, adjusting a location of the computer-readable reconstruction of the trace superimposed on the computer-readable reconstruction of the implant at 1023, displaying the computer-readable reconstruction of the trace at 1025, tracing the projected computer-readable reconstruction of the trace on the implant with a marking tool at 1027, and removing excess material from the implant to form a resized implant at 1029. The surgical method 1000 may include implant attachment at 1007 which includes placing the resized implant at an osteotomy site at 1031 (which may be the location where the portion of the being's anatomy was resected at 1013) and attaching the resized implant to the being's anatomy at 1033, which may be done with plates, screws or a combination thereof.

Figure 11:
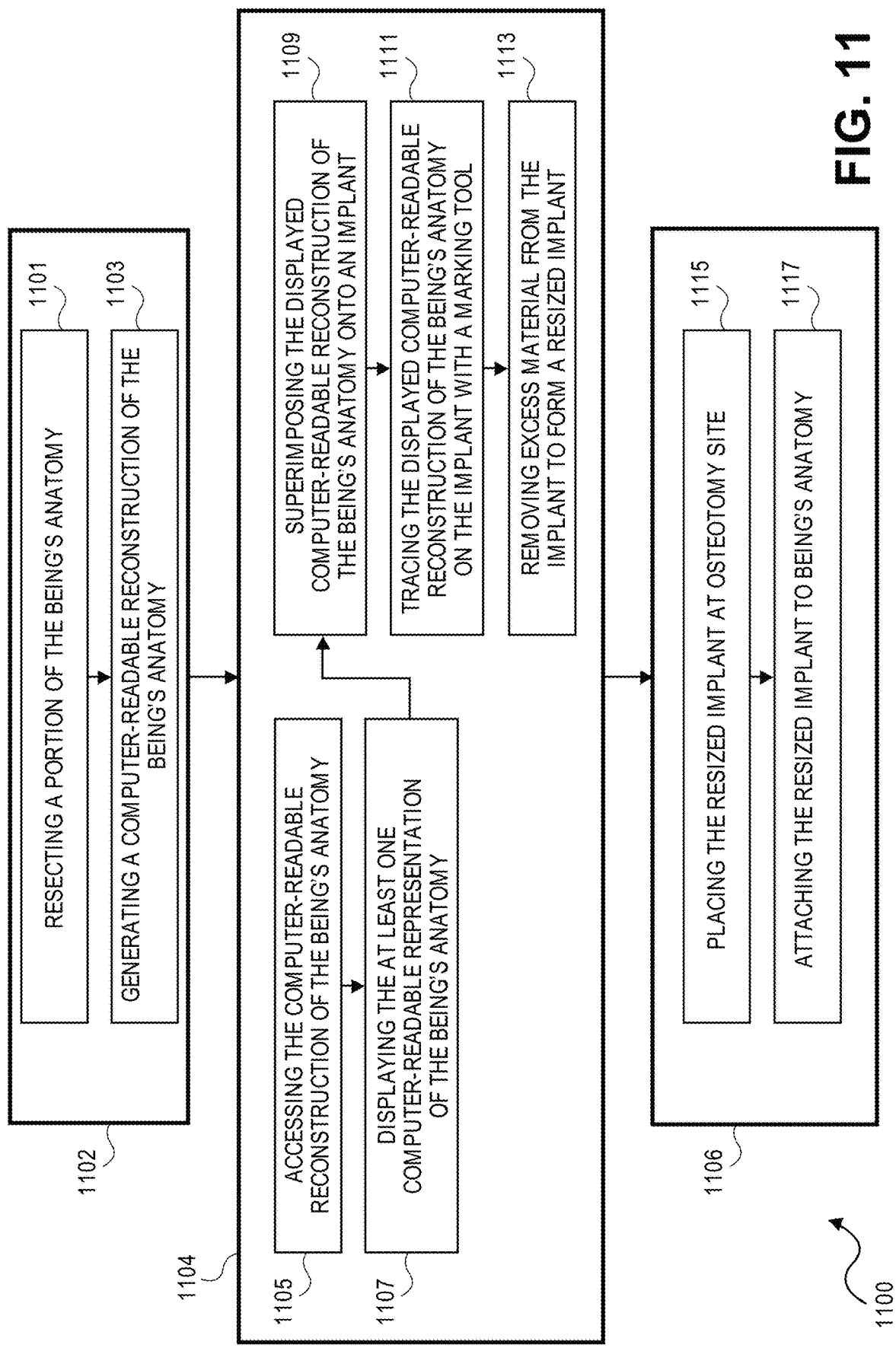
FIG. 11 is a flow chart depicting an embodiment of a surgical method which can be executed for sizing an implant to an anatomical feature.

The methods, tools and systems described with respect to, for example, FIGS. 7-9 may be included in a surgical method, such as surgical method 1100 of FIG. 11 which can be executed for sizing an implant to an anatomical feature. Surgical method 1100 may include one or more of a surgical procedure 1102, an implant modification 1104 and an implant attachment 1106. The surgical method 1100 may include surgical procedure 1102 which includes one or more of resecting a portion of the beings anatomy at 1101, tracing and generating a computer-readable reconstruction of the being's anatomy at 1103. Surgical method 1100 may include implant modification 1104 which includes accessing the computer-readable reconstruction of the being's anatomy at 1105, displaying the at least one computer-readable reconstruction of the being's anatomy at 1107, superimposing the displayed computer-readable reconstruction of the being's anatomy onto an implant at 1109, tracing the displayed computer-readable reconstruction of the being's anatomy on the implant with a marking tool at 1111, and removing excess material from the implant to form a resized implant at 1113. The surgical method 1100 may include implant attachment 1106 which includes placing the resized implant at an osteotomy site at 1115 (which may be the location where the portion of the being's anatomy was resected at 1101) and attaching the resized implant to the being's anatomy at 1117, which may be done with plates, screws or a combination thereof.

EXAMPLES

Example 1—Comparison Between Conventional Method ("Control Surgery—Cadaver 1) and a Method of the Embodiments ("Experimental Surgery—Cadaver #2)

Identical defects were created on two male cadaver heads (cadaver #1 and cadaver #2) to mimic skull neoplasm resection. For cadaver #1, a conventional method for reducing the size of an implant includes hand-drawing an outline for later drill shaving. This conventional method required the surgeon to use his eyes and hands to judge on where the implant requires modification in order to fit the implant within the skull defect. While custom cranial implants are beneficial, the conventional method required intra-op modifications and in this particular instance took a total time of around 35 minutes. The conventional method for modifying an oversized custom-cranial implant resulted in suboptimal bone-to-implant gaps (verified in 3D CT post-op scan image).

For cadaver #2, a method of an embodiment was used to modify a CCI. A similar defect was created on cadaver #2 as was for cadaver #1. CAPE system hardware, including a cranial mount and a trackable position indicator were attached to the cadaver #2 for intra-op assessment of exact defect size to guide real-time implant modification. Fiducial registration was performed via an on-screen image with a CT-scan that was preuploaded. The trackable components of the CAPE system were tracked with an optical tracker (POLARIS). A modified implant was formed, for example, according to a method of an embodiment. A red light, corresponding to a geometry of a trace as described above, was projected onto the implant for guiding the surgeon on marking areas for further customization of the implant. A sterile marking pen was used for outlining/marking on the projected trace. Excess portions of the implant, defined by those portions outside of a boundary of the outlined/marked trace, were removed and the implant was attached onto the cadaver via rigid fixation. This experimental surgery on Cadaver #2 required only 3 minutes for total implant customization time and resulted in acceptable bone-to implant gaps.

Example 2 Comparison Between Conventional Method ("Control Technique—Cadaver #1) and Computer-Assisted Craniomaxillofacial Surgical Method of the Embodiments ("Experimental Surgery—Cadavers #2-6)

A total of 6 single-stage cranioplasties with CCIs were performed on cadaveric specimens obtained through the Maryland State Anatomy Board. The first surgery on cadaver #1, served as the control method, and was performed via standard technique which required the surgeon to use his eyes and hands to judge the locations of the implant that required modification in order to fit the skull defect. For objective comparison, the next 5 experimental surgeries (on cadavers #2-#6) utilized the novel computer-assisted methods of the embodiments.

For the purpose of qualitative and quantitative post-surgical analyses, pre- and post-operative CT scans were obtained throughout the six experiments on all six cadavers; each cadaver specimen underwent three CT scans each. A SOMATOM Definition Flash (Siemens Healthcare; Germany) at 0.48×0.48×0.50 mm3 resolution was used to identify the existing skeletal anatomy—and all scans were labeled either "pre-defect", "pre-cranioplasty" or "post-cranioplasty". Of note, varying skull defects were manually created simulating previous skull tumors located around the anterior skull region. Automated thresholding in Mimics (Materialise; Plymouth, MI) generated surface models of each scan (n=5). From these post-trauma models, oversized CCI's were designed and printed using additive manufacturing techniques for each of the six cadaver specimens. For the conventional method, the CCI for cadaver #1 was trimmed using "hand and eye guidance" only.

For the method of the embodiments, the surgeon (CRG) registered each of the cadavers #2-#6 skulls intra-operatively and digitized the respective defect outline following the methods described in the above-embodiments and oncological resection. Following digitization, an overhead projector displayed the skeletal defect outline onto the implant (without any direct contact risking contamination) using a thin laser and red beam of light, which then allowed the surgeon to trace the irregular borderline with a sterile marking pen. For all six cases, the implant was cut to size using a handheld burr and attached to the specimen's skeleton with standard fixation plates and screws. The operations were timed in segments, including the reference fixation and implant modification times. Post-operative CT scans of the specimens recorded the final outcome for both quantitative and qualitative analyses.

Commercial image processing software—Amira (Visualization Sciences Group; Burlington, MA)—provided segmentation and visualization for post-hoc analysis of all six CCI cranioplasties. Registration using normalized mutual information in Amira aligned the pre-operative and post-defect CT volumes together. A binary masking operation between manually labeled volumes of the "pre-op" and "pre-cranioplasty" CT scans was performed to identify the true defect size and shape. After aligning the post-operative CT volumes to the pre-operative volumes, a threshold-based segmentation with manual refinement separated the implants from the bone on all post-operative scans. The Amira software was used to generate surface models of the corresponding implants and the defects. Since implant thickness did not match skull thickness, only the "top" surfaces of each model were considered. A distance map measured the similarity between the implants and defects by identifying the closest point on the implant for each vertex of the defect surface.

The conventional method and the method of the embodiments were quantified objectively with "total time saved" and "total time used" through various parts of the surgeries (n=6). The "standard control method" required around 35 minutes for intra-op modification, which is highly consistent with average times reported in the literature for single-stage CCI reconstruction. More importantly, the labor-intense "control method" also resulted in suboptimal bone-to-implant gaps at the perimeter of the tumor defect. The conventional method's inaccuracy was demonstrated on a post-cranioplasty 3D CT scan image. In contrast, all five experimental surgeries (n=5) performed according the surgical methods of the embodiments showed significant time reduction and improved accuracy—with stepwise success as the study progressed during a nine month time span. Most notably, the experimental surgeries performed according to methods of the embodiments using computer-assistance (i.e., surgeries for Cadavers #2-6) required, on average, only 3-4 minutes in total for implant customization—which is a staggering time reduction of around 90-95%. More impressively, minimized bone-to implant gaps were observed, which equates to an improved cranial reconstruction and aesthetic result.

Implants resized according to the methods of the embodiments fit very well in their respective defect, with improved positioning as compared to the control/conventional method. For example, all cadavers #2-#6 showed that the entire top surface of the implant was placed properly within about 1 mm, on average, of the original skull defect. Actual results are shown in Table 1 for all surgeries.

TABLE 1

| Cadaver ID | | 2 | 3 | 4 | 5 | 6 | Mean |
|---|---|---|---|---|---|---|---|
| Timing (sec) | Ref mounting | 144 | 270 | 120 | 124 | 124 | 156.4 |
| | Registration + tracing | 140 | 135 | 160 | 106 | 180 | 144.2 |
| | Implant tracing | 80 | 61 | n/a | 35.6 | 60 | 59.2 |
| | Cutting Mount | 460 | 435 | n/a | 126 | 217.6 | 309.7 |
| | Removal | | | | 48 | 48 | 48 |
| | Total | 824 | 901 | 280 | 439.6 | 629.6 | 614.8 |

TABLE 1-continued

| Cadaver ID | | 2 | 3 | 4 | 5 | 6 | Mean |
|---|---|---|---|---|---|---|---|
| Software Time (sec) | | | | | 60 | | 60 |
| Distance on defect (mm) | Mean | 1.06 | 0.74 | 0.92 | 0.98 | 1.28 | 0.996 |
| | Std | 1.33 | 0.67 | 0.48 | 1.16 | 1.40 | |
| | Max | 10.29 | 4.79 | 2.46 | 8.07 | 8.39 | |
| Distance on implant (mm) | Mean | 0.74 | 0.67 | 0.92 | 0.52 | 0.68 | 0.706 |
| | Std | 0.60 | 0.62 | 0.48 | 0.40 | 0.53 | |
| | Max | 2.98 | 4.99 | 2.46 | 2.65 | 3.85 | |
| Surface Area (mm2) | Initial | 14263.90 | 12431.50 | 20081.30 | 18379.90 | 22003.30 | 17431.38 |
| | Final | 7682.58 | 5523.24 | 8129.26 | 6504.21 | 7491.27 | 7066.11 |
| Intraop Registration (m) | Mean | 1.49 | 0.25 | 0.31 | 0.76 | 0.65 | 0.692 |
| | Std | 1.14 | 0.19 | 0.28 | 0.58 | 0.39 | |
| | Max | 4.66 | 0.87 | 1.80 | 2.89 | 1.96 | |
| Notes | | Revision | Revision | Revision | No revision | No revision | |

In summary, the surgeries performed according to the surgical methods of the embodiments showed unequivocal success in achieving its milestones, by drastically reducing the time necessary for single-stage cranioplasty reconstruction, and at the same time, significantly improving the implant modification for an ideal fit.

As used herein, to the extent that the terms "coupled," "connected," and "connecting", or variants thereof are used in either the detailed description and the claims, such terms are intended to refer to "in direct connection with" or "in connection with via one or more intermediate elements or members." As used herein, to the extent that the terms "including", "includes", "having", "has", "with", or variants thereof are used in either the detailed description and the claims, such terms are intended to be inclusive in a manner similar to the term "comprising." As used herein, the phrase "at least one of" or "one or more of", for example, A, B, and C means any of the following: either A, B, or C alone; or combinations of two, such as A and B, B and C, and A and C; or combinations of three A, B and C.

Other embodiments will be apparent to those skilled in the art from consideration of the specification and practice of the examples disclosed herein. It is intended that the specification and examples be considered as exemplary only, with a true scope and spirit of the embodiments being indicated by the following claims.

What is claimed is:

1. A method of sizing a surgical implant to an anatomical feature characterized in part by a missing or malformed portion in a cranioplasty, the method comprising:
   generating at least one computer-readable reconstruction of the anatomical feature with a source, wherein the at least one computer-readable reconstruction of the anatomical feature includes position information corresponding to an orientation of the source, wherein the being's anatomy comprises a skull;
   accessing the at least one computer-readable reconstruction of the being's anatomy and position information;
   displaying an image based on the at least one computer-readable reconstruction of the anatomical feature and the position information; and
   projecting the image onto a surface of the surgical implant, wherein a surgeon traces the image with a sterile marking pen directly onto the surface of the surgical implant to outline projected points of the anatomical feature in the image onto corresponding physical locations on the surface of the surgical implant, and wherein the projecting is performed using a projector device.

2. The method of claim 1, wherein the at least one computer-readable reconstruction of the being's anatomy comprises a plurality of digital images, wherein at least one of the plurality of digital images is associated with the position information.

3. The method of claim 2, further comprising stitching the plurality of digital images together to form the computer-readable reconstruction of the being's anatomy.

4. The method of claim 1, wherein the source that generates the at least one computer-readable reconstruction of the being's anatomy is a camera.

5. The method of claim 4, wherein the camera is a Red Green Blue (RGB) camera.

6. The method of claim 1, wherein the source that generates the at least one computer-readable reconstruction of the being's anatomy is a depth sensor.

7. The method of claim 1, wherein the source that generates the at least one computer-readable reconstruction of the being's anatomy is a combination of a depth sensor and a camera.

8. The method of claim 1, wherein the source that generates the at least one computer-readable reconstruction of the being's anatomy is a laser scanning device.

* * * * *